United States Patent
Maurer et al.

(10) Patent No.: US 10,537,624 B2
(45) Date of Patent: Jan. 21, 2020

(54) TRANSFECTED T-CELLS AND T-CELL RECEPTORS FOR USE IN IMMUNOTHERAPY AGAINST CANCERS

(71) Applicant: IMMATICS BIOTECHNOLOGIES GMBH, Tuebingen (DE)

(72) Inventors: Dominik Maurer, Moessingen (DE); Leonie Alten, Tuebingen (DE); Sebastian Bunk, Tuebingen (DE)

(73) Assignee: Immatics Biotechnologies GmbH, Tuebingen (DE)

( * ) Notice: Subject to any disclaimer, the term of this patent is extended or adjusted under 35 U.S.C. 154(b) by 189 days.

(21) Appl. No.: 15/461,020

(22) Filed: Mar. 16, 2017

(65) Prior Publication Data

US 2017/0312350 A1 Nov. 2, 2017

Related U.S. Application Data

(60) Provisional application No. 62/308,970, filed on Mar. 16, 2016.

(30) Foreign Application Priority Data

Mar. 16, 2016 (GB) .................... 1604494.3

(51) Int. Cl.
*C07K 14/725* (2006.01)
*A61K 39/00* (2006.01)
*A61K 45/06* (2006.01)
*G01N 33/574* (2006.01)

(52) U.S. Cl.
CPC .......... *A61K 39/0011* (2013.01); *A61K 45/06* (2013.01); *C07K 14/7051* (2013.01); *G01N 33/574* (2013.01); *A61K 2039/5158* (2013.01); *C07K 2319/00* (2013.01)

(58) Field of Classification Search
None
See application file for complete search history.

(56) References Cited

U.S. PATENT DOCUMENTS

2012/0308590 A1 12/2012 Nishimura et al.
2015/0125477 A1 5/2015 Kuttruff-Coqui et al.

FOREIGN PATENT DOCUMENTS

| EP | 1930433 A | 6/2008 |
|---|---|---|
| EP | 2172211 A1 | 4/2010 |
| WO | 2011/067920 A1 | 6/2011 |
| WO | 2015/063302 A2 | 5/2015 |

OTHER PUBLICATIONS

Office Action dated May 1, 2019, in connection with related Moroccan Patent Application No. 43328.
Tomita et al., "Peptides derived from human insulin-like growth factor-II mRNA binding protein 3 can induce human leukocyte antigen-A2-restricted cytotoxic T lymphocytes reactive to cancer cells." Cancer Science, Japanese Cancer Association, Tokyo, JP DOI: 10.1111/J.1349-7006.2010.01780.X.
Tomita et al. "Peptides derived from human insulin-like growth factor-II mRNA binding protein 3 can induce human leukocyte antigen-A2-restricted cytotoxic T lymphocytes reactive to cancer cells", Cancer Sci (2011), vol. 102 No. 1, pp. 71-78.
Search Report of GB1604494.3 dated Dec. 30, 2016.

*Primary Examiner* — Zachary S Skelding
(74) *Attorney, Agent, or Firm* — McBee Moore Woodward & Vanik IP, LLC

(57) ABSTRACT

The present description relates to T-cell receptors (TCRs) binding to tumor-associated antigens (TAAs) for targeting cancer cells, T-cells expressing same, methods for producing same, and methods for treating cancers using same. In particular, the present description relates to TCRs and their variants that bind to HLA class I or II molecules with a peptide, such as IGF2BP3-001 have the amino acid sequence of KIQEILTQV (SEQ ID NO:1). The present description further relates to peptides, proteins, nucleic acids and cells for use in immunotherapeutic methods. In particular, the present description relates to the immunotherapy of cancer. The present description furthermore relates to tumor-associated T-cell peptide epitopes, alone or in combination with other tumor-associated peptides that can for example serve as active pharmaceutical ingredients of vaccine compositions that stimulate anti-tumor immune responses, or to stimulate T-cells ex vivo and transfer into patients. Peptides bound to molecules of the major histocompatibility complex (MHC), or peptides as such, can also be targets of antibodies, soluble T-cell receptors, and other binding molecules.

13 Claims, 8 Drawing Sheets

Specification includes a Sequence Listing.

US 10,537,624 B2

TRANSFECTED T-CELLS AND T-CELL RECEPTORS FOR USE IN IMMUNOTHERAPY AGAINST CANCERS

CROSS REFERENCE TO RELATED APPLICATIONS

This application claims the benefit of U.S. Provisional Application Ser. No. 62/308,975, filed 16 Mar. 2016, and Great Britain Application No. 1604494.3, filed 16 Mar. 2016, the content of each of these applications is herein incorporated by reference in their entirety.

This application also is related to PCT/EP2017/056289 filed 16 Mar. 2017, the content of which is incorporated herein by reference in its entirety.

REFERENCE TO SEQUENCE LISTING SUBMITTED AS A COMPLIANT ASCII TEXT FILE (.txt)

Pursuant to the EFS-Web legal framework and 37 CFR §§ 1.821-825 (see MPEP § 2442.03(a)), a Sequence Listing in the form of an ASCII-compliant text file (entitled "Sequence_Listing_2912919-065001_ST25.txt" created on 15 Mar. 2016, and 20,310 bytes in size) is submitted concurrently with the instant application, and the entire contents of the Sequence Listing are incorporated herein by reference.

BACKGROUND

T-cell based immunotherapy targets peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defect ribosomal products (DRIPS) located in the cytosol, play an important role in this response. The MHC-molecules of the human are also designated as human leukocyte-antigens (HLA).

IGF2BP3 is a member of the insulin-like growth factor-II mRNA-binding protein family, implicated in mRNA localization, turnover and translational control. The presence of high transcript levels of IGF2BP3 in numerous cancer tissues as compared to control tissues indicates that the IGF2BP3 protein might play a functional role in proliferating transformed cells. IGF2BP3 expression has been reported in a number of cancer types, including clear cell renal cell carcinoma (RCC); malignant melanoma; esophageal squamous cell carcinoma; pancreatic carcinoma; and urothelial tumors. Thus, epitopes derived from IGF2BP3 may be useful for targeting anti-cancer therapeutics to IGF2BP3-expressing cancers.

There are two classes of MHC-molecules, MHC class I and MHC class II. Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies.

In the MHC class I dependent immune reaction, peptides not only have to be able to bind to certain MHC class I molecules expressed by tumor cells, they subsequently also have to be recognized by T-cells bearing specific T-cell receptors (TCR). Therefore, TAAs are a starting point for the development of a T-cell based therapy including but not limited to tumor vaccines and cell therapies.

While advances have been made in the development of molecular-targeting drugs for cancer therapy, there remains a need in the art to develop new anti-cancer agents that specifically target molecules highly specific to cancer cells. The present description addresses that need by providing novel TCRs, nucleic acids, vectors and host cells which specifically bind to epitopes of IGF2BP3 such as the peptide KIQEILTQV (IGF2BP3-001; SEQ ID NO:1) and variants thereof; and methods of using such molecules in the treatment of cancer.

SUMMARY

The present description relates to T-cell receptors (TCRs) comprising an alpha chain and a beta chain ("alpha/beta TCRs"). In another embodiment, the present description relates to TCRs comprising a gamma chain and delta chain ("gamma/delta TCRs").

The present description further relates to TCRs, individual TCR subunits (alone or in combination), and subdomains thereof, soluble TCRs (sTCRs), for example, soluble alpha/beta dimeric TCRs having at least one disulfide interchain bond between constant domain residues that are not present in native TCRs, and cloned TCRs, said TCRs engineered into autologous or allogeneic T-cells or T-cell progenitor cells, and methods of making same, as well as other cells bearing said TCR.

The present description further relates to a TCR that specifically binds to an IGF2BP3-001 peptide-HLA molecule complex, wherein the IGF2BP3-001 peptide comprises, or alternatively consists of, KIQEILTQV (SEQ ID NO:1). In an embodiment the HLA molecule is HLA-A*02.

The present description further relates to a TCR that specifically binds to a IGF2BP3-001 peptide-HLA molecule complex, wherein the IGF2BP3-001 peptide comprises, or alternatively consists of, a variant of the IGF2BP3-001 which is at least 66%, preferably at least 77%, and more preferably at least 88% homologous (preferably at least 77% or at least 88% identical) to SEQ ID NO:1, wherein said variant binds to an HLA class I or class II molecule and/or induces T-cells cross-reacting with said peptide, or a pharmaceutically acceptable salt thereof, wherein said peptide is not the underlying full-length polypeptide.

The present description further relates to a peptide of the present description comprising a sequence that is selected from the group consisting of SEQ ID NO:1 or a variant thereof, which is at least 66%, preferably at least 77%, and more preferably at least 88% homologous (preferably at least 77% or at least 88% identical) to SEQ ID NO:1, wherein said peptide or variant thereof has an overall length of between 8 and 100, preferably between 8 and 30, and most preferably of between 8 and 14 amino acids.

The present description further relates to TCRs comprising a TCR alpha variable domain that has at least 75%, 80%, 90%, 95%, 98%, or 99% sequence identity, preferably 90% sequence identity, to a TCR alpha variable domain shown in Table 1; and the TCR beta variable domain has at least at least 75%, 80%, 90%, 95%, 98%, or 99% sequence identity, preferably 90% sequence identity, to a TCR beta variable domain shown in Table 1.

In an embodiment, the TCR alpha variable domain has at least one mutation relative to a TCR alpha domain shown in Table 1; and/or the TCR beta variable domain has at least one mutation relative to a TCR alpha domain shown in Table 1. In an embodiment, a TCR comprising at least one mutation in the TCR alpha variable domain and/or TCR beta variable domain has a binding affinity for, and/or a binding half-life for, an IGF2BP3-001 peptide-HLA molecule complex, which is at least double that of a TCR comprising the unmutated TCR alpha domain and/or unmutated TCR beta variable domain.

The TCR alpha chains of the present description may further comprise a TCR alpha constant domain that has at least 70%, 75%, 80%, 90%, 95%, 98%, or 99% sequence identity to a TCR alpha constant domain shown in Table 1. The TCR beta chains of the present description may further comprise a TCR beta constant domain that has at least 70%, 75%, 80%, 90%, 95%, 98%, or 99% sequence identity to a TCR beta constant domain shown in Table 1.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The description further relates to TCR alpha chains comprising one or more alpha chain complementarity determining regions (CDRs) disclosed in Table 1, and variants thereof having one, two, three or four substitutions relative to the CDRs shown in Table 1. Further described are TCR alpha chains comprising at least one CDR selected from a CDR1, CDR2 and CDR3 shown in Table 1. Further described are TCR alpha chains comprising an alpha chain CDR3 shown in Table 1.

The description further relates to TCR beta chains comprising one or more beta chain complementarity determining regions (CDRs) disclosed in Table 1, and variants thereof having one, two, three or four substitutions relative to the CDRs shown in Table 1. Further described are TCR beta chains comprising at least one CDR selected from a beta chain CDR1, CDR2 and CDR3 shown in Table 1. Further described are TCR beta chains comprising a beta chain CDR3 shown in Table 1.

The description further relates to an isolated or recombinant nucleic acid comprising a nucleotide sequence encoding a TCR of the present description. In an embodiment, nucleic acids of the description encode a TCR alpha chain and/or a TCR beta chain as shown in Table 1.

The description further relates to a recombinant expression vector comprising a nucleic acid encoding a TCR alpha chain, beta chain, or both, as described herein.

The description further relates to an isolated host cell comprising a recombinant expression vector expressing a nucleic acid encoding the TCR alpha chain, beta chain, or both, as described herein.

The description further relates to an isolated host cell comprising a recombinant expression vector according to the present description, preferably wherein the cell is a human cell, preferably a peripheral blood lymphocyte (PBL), more preferably a CD4 or CD8 positive T lymphocyte.

The description further relates to an isolated PBL comprising the recombinant expression vector of the description, wherein the PBL is a CD8+ T-cell or a CD4+ T-cell.

The description further relates to a population of cells comprising at least one host cell described herein.

The description further relates to TCRs and host cells of the present description for use in the treatment of proliferative diseases, such as, non-small cell lung cancer, small cell lung cancer, renal cell cancer, brain cancer (e.g., glioblastoma, neuroblastoma), gastric cancer, colorectal cancer, hepatocellular cancer, head and neck cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

In an aspect, the host cell is a CD8+ T-cell or a CD4+ T-cell transfected with a nucleic acid encoding at least one TCR according to the description, wherein the TCR comprises at least one amino acid sequence disclosed in Table 1. In another aspect such host cells are used in the immunotherapy of small cell lung cancer, non-small cell lung cancer, small cell lung cancer, renal cell cancer, brain cancer (e.g., glioblastoma, neuroblastoma), gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The description further relates to methods of killing or reducing the number of cancer cells comprising contacting the cancer cells with a TCR, nucleic acid, vector or host cell as described herein. Also provided are methods of treating cancer comprising administering to a subject in need thereof a TCR, nucleic acid, vector or host cell as described herein.

The description further relates to a nucleic acid encoding a TCR according to the description, and expression vector capable of expressing a nucleic acid according to the description.

The description further relates to a TCR according to the description, a nucleic acid according to the description or an expression vector according to the description for use in the treatment of diseases and in medicine, in particular in the treatment of cancer.

The description further relates to a host cell comprising a nucleic acid according to the description or an expression vector as described before.

The description further relates to the host cell according to the description that is an antigen presenting cell, and preferably is a dendritic cell.

The description further relates to a method for producing a peptide according to the description, the method comprising culturing the host cell according to the description, and isolating the peptide from said host cell or its culture medium.

The description further relates to methods according to the description, wherein the antigen is loaded onto class I or II MHC molecules expressed on the surface of a suitable antigen-presenting cell or artificial antigen-presenting cell by contacting a sufficient amount of the antigen with an antigen-presenting cell or the antigen is loaded onto class I or II MHC tetramers by tetramerizing the antigen/class I or II MHC complex monomers.

The description further relates to the method according to the description, wherein the antigen-presenting cell comprises an expression vector capable of expressing or expressing said peptide containing SEQ ID NO:1 or a variant thereof.

The description further relates to activated T-lymphocytes, produced by the method according to the description, wherein a T-cell selectively recognizes a cell which expresses a polypeptide comprising an amino acid sequence according to the description.

The description further relates to methods of killing cancer and/or suppressing cells in a patient which cancer cells aberrantly express a polypeptide comprising any amino acid sequence according to the description, the methods comprising administering to the patient an effective number of T-cells as produced according to the description.

The description further relates to the use of any peptide described herein, nucleic acids according described herein, expression vectors described herein, cells described herein, activated T lymphocyte described herein, T-cell receptors, antibodies, or other peptide- and/or peptide-MHC-binding molecules according to the present description as a medicament or in the manufacture of a medicament. In an aspect, the medicament is active against cancer.

Preferably, said medicament is a cellular therapy, a TCR, a soluble TCR or antibody.

The present description further relates to a use according to the present description, wherein the cancer cells are non-small cell lung cancer, small cell lung cancer, renal cell cancer, brain cancer (e.g., glioblastoma, neuroblastoma), gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer, and preferably non-small cell lung cancer.

The present description further relates to biomarkers based on the peptides according to the present description, herein called "targets," that can be used in the diagnosis of cancer, preferably non-small cell lung cancer. The marker can be the over-presentation of the peptide(s) themselves, or over-expression of the corresponding gene(s). The markers may also be used to predict the probability of success of a treatment, preferably an immunotherapy, and most preferred an immunotherapy targeting the same target that is identified by the biomarker. For example, an antibody or soluble TCR can be used to stain sections of the tumor to detect the presence of a peptide of interest in complex with MHC. Optionally the antibody or soluble TCR carries a further effector function such as an immune stimulating domain or toxin.

The present description further relates to the use of these novel targets for the identification of TCRs that recognize at least one of said targets, and preferably the identification of said TCRs that activate T-cells.

The present description also relates to the use of these novel targets in the context of cancer treatment.

DETAILED DESCRIPTION

Figure 1:
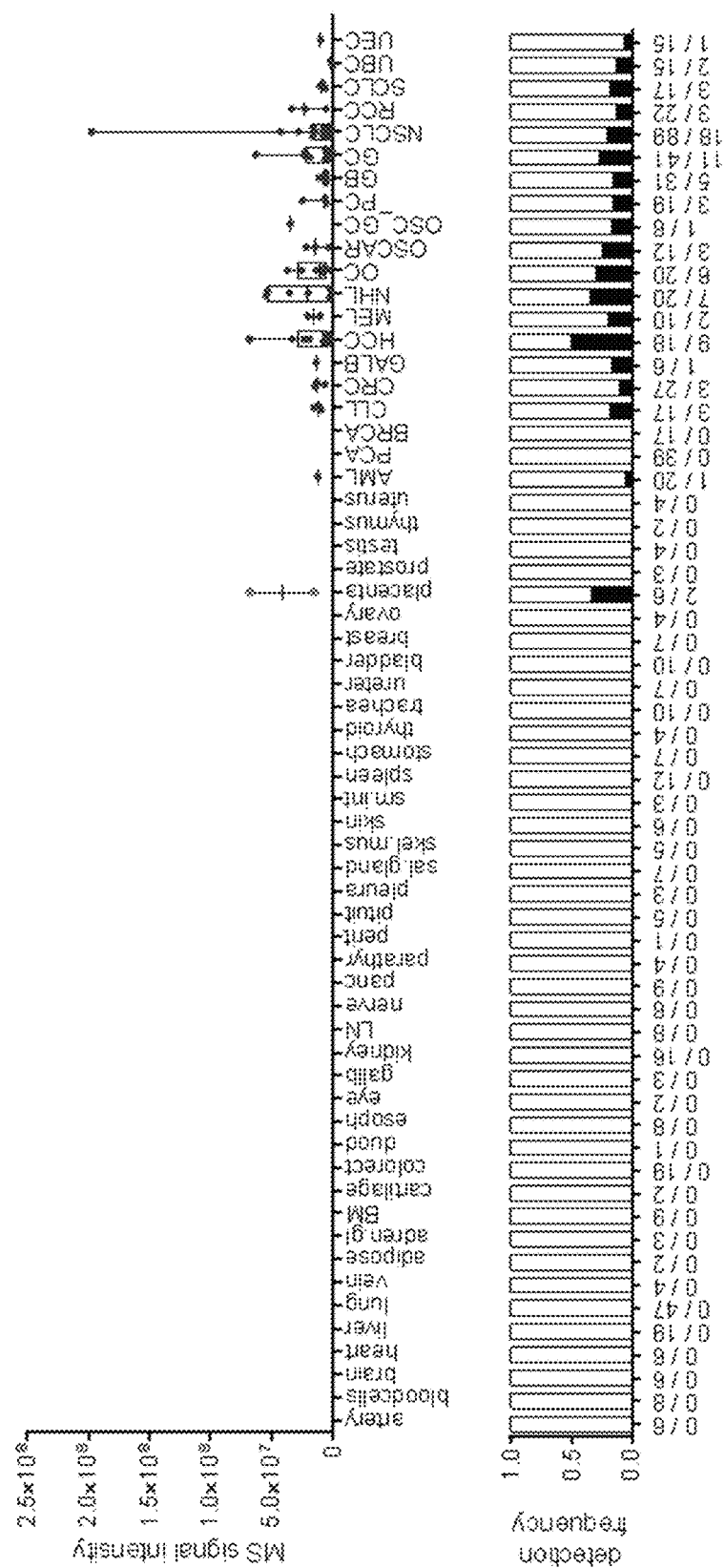
FIG. 1 shows IGF2BP3-001 peptide presentation in healthy tissues and cancers.
Figure 2:
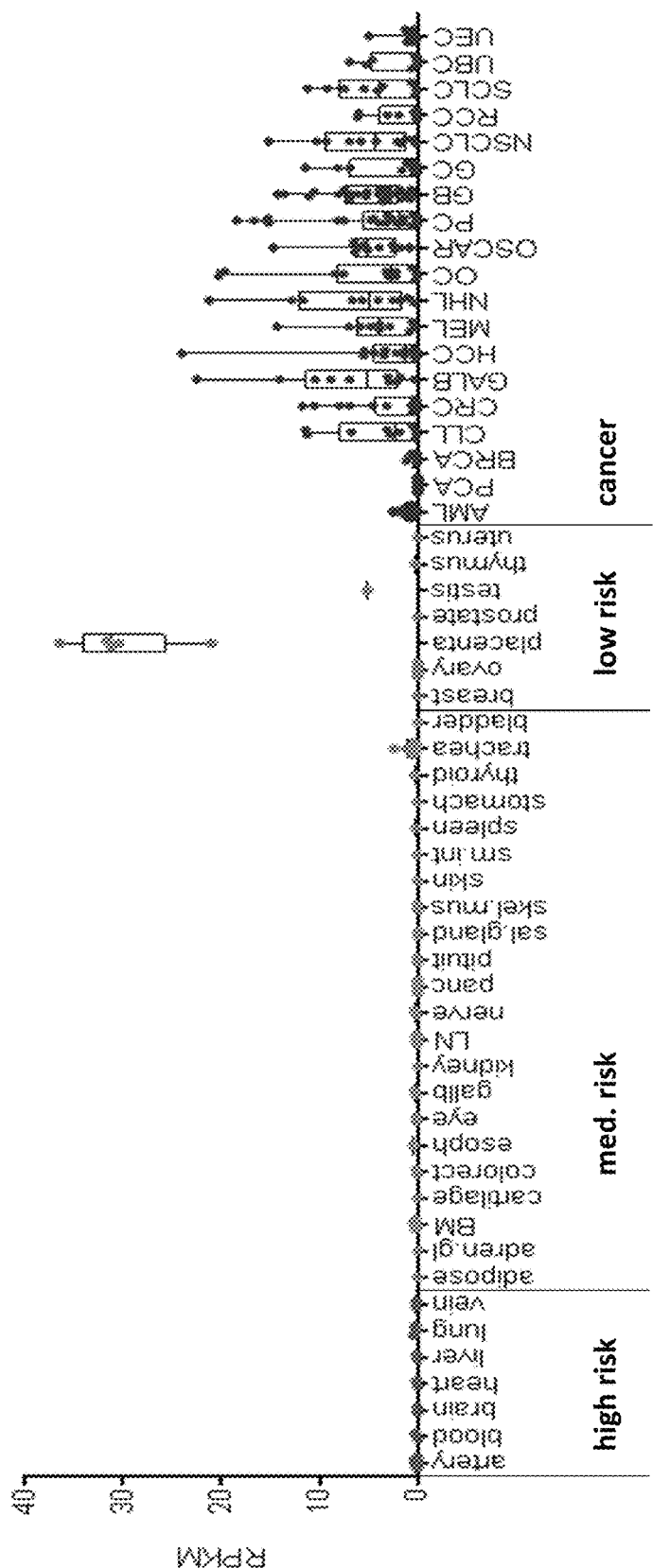
FIG. 2 shows IGF2BP3-001 expression in cancer and healthy tissues.
Figure 3:
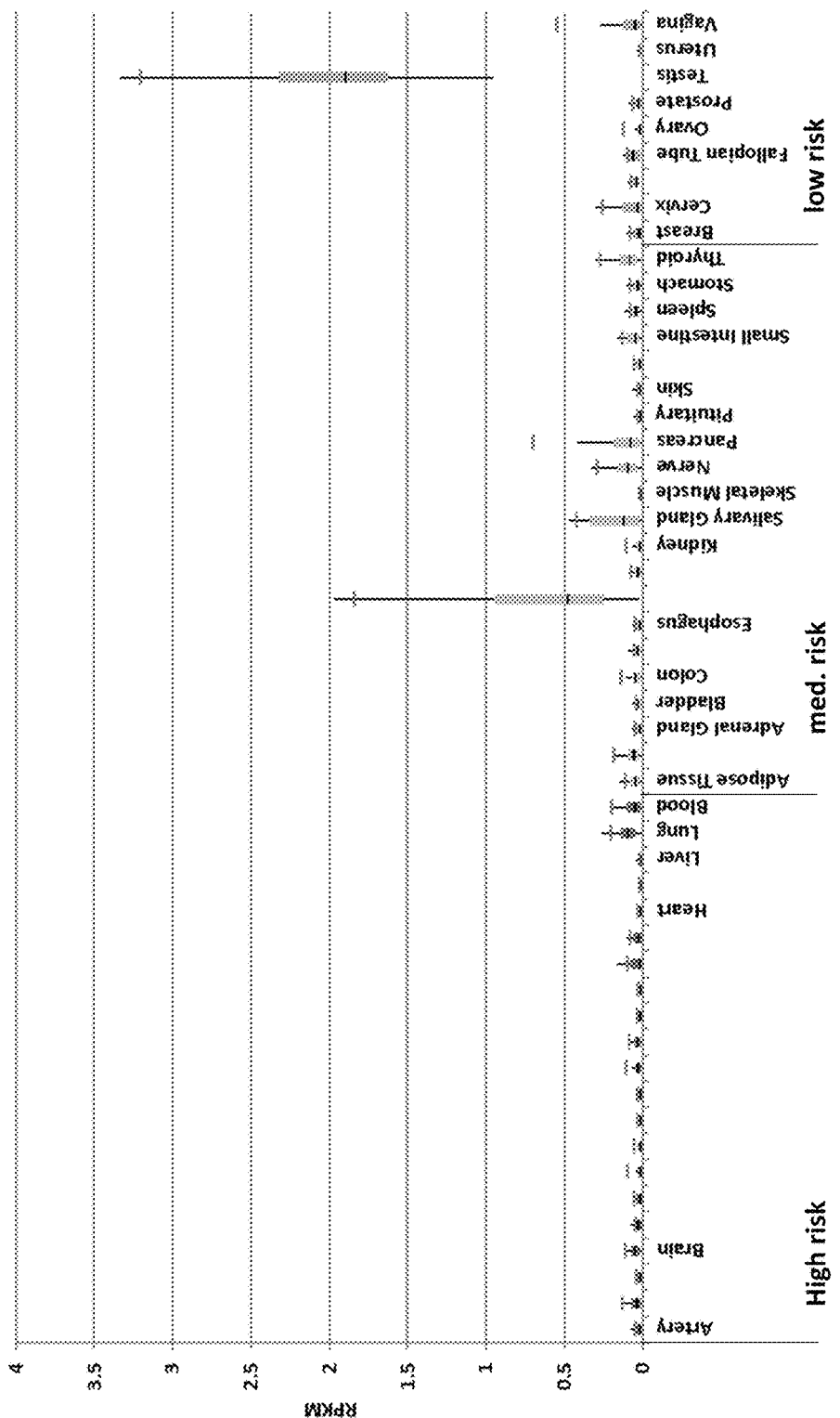
FIG. 3 shows IGF2BP3-001 expression in cancer and healthy tissues.
Figure 4:
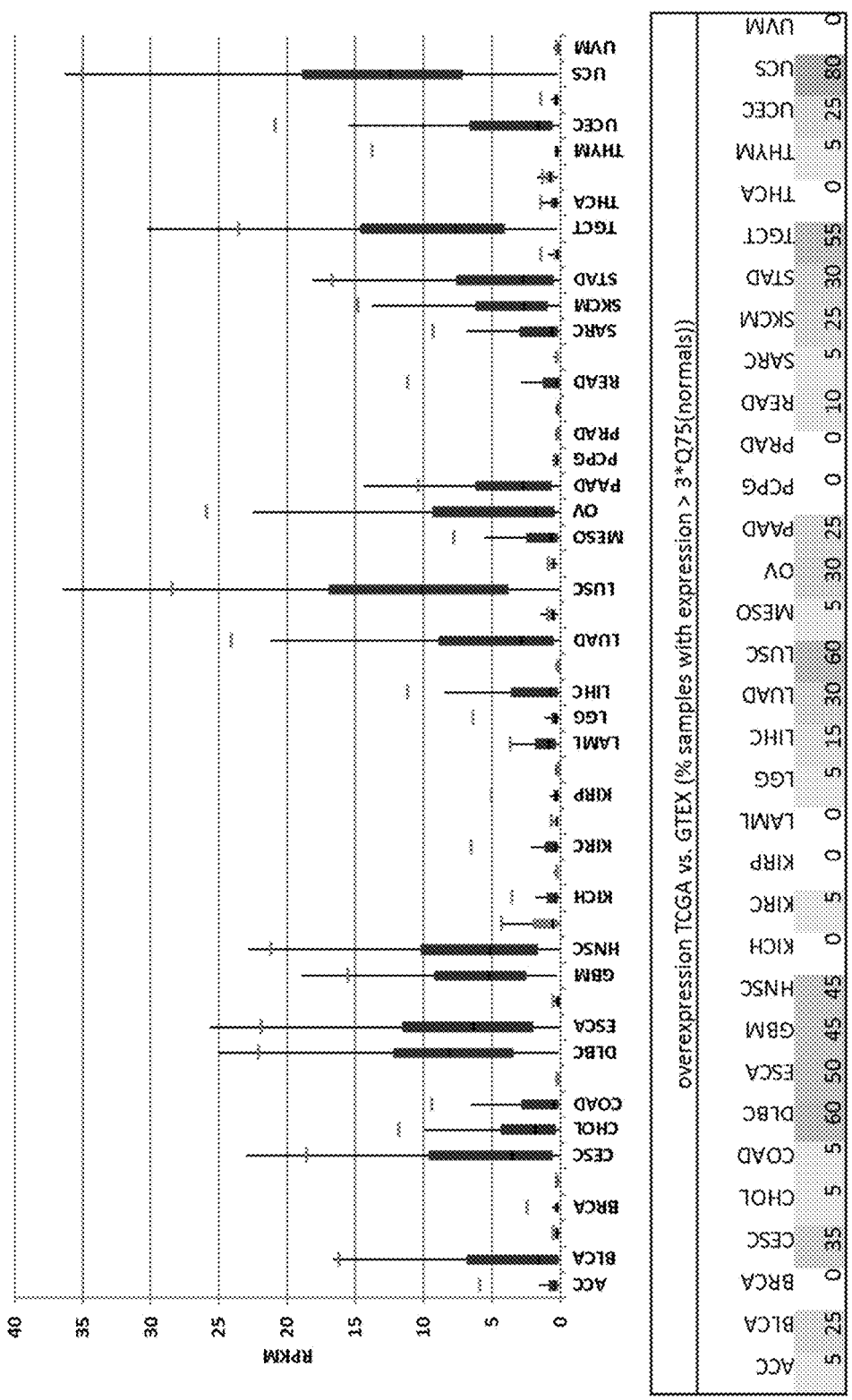
FIG. 4 shows IGF2BP3-001 expression in cancer and healthy tissues.

The present description relates to T-cell receptors (TCRs) comprising an alpha chain and a beta chain ("alpha/beta TCRs"). Also provided are IGF2BP3-001 peptides capable of binding to TCRs and antibodies when presented by an MHC molecule. The present description also relates to nucleic acids, vectors and host cells for expressing TCRs and peptides of the present description; and methods of using the same.

Definitions

As used herein and except as noted otherwise all terms are defined as given below.

The term "T-cell receptor" (abbreviated TCR) refers to a heterodimeric molecule comprising an alpha polypeptide chain (alpha chain) and a beta polypeptide chain (beta chain), wherein the heterodimeric receptor is capable of binding to a peptide antigen presented by an HLA molecule.

The term "T-cell response" means the specific proliferation and activation of effector functions induced by a peptide in vitro or in vivo. For MHC class I restricted cytotoxic T-cells, effector functions may be lysis of peptide-pulsed, peptide-precursor pulsed or naturally peptide-presenting target-cells, secretion of cytokines, preferably Interferon-gamma, TNF-alpha, or IL-2 induced by peptide, secretion of effector molecules, preferably granzymes or perforins induced by peptide, or degranulation.

The term "peptide" is used herein to designate a series of amino acid residues, connected one to the other typically by peptide bonds between the alpha-amino and carbonyl groups of the adjacent amino acids. The peptides are preferably 9 amino acids in length, but can be as short as 8 amino acids in length, and as long as 10, 11, or 12 or longer, and in case of MHC class II peptides (longer variants of the peptides of the description) they can be as long as 13, 14, 15, 16, 17, 18, 19 or 20 or more amino acids in length.

Furthermore, the term "peptide" shall include salts of a series of amino acid residues, connected one to the other typically by peptide bonds between the alpha-amino and carbonyl groups of the adjacent amino acids. Preferably, the salts are pharmaceutical acceptable salts of the peptides, such as, for example, the chloride or acetate (trifluoroacetate) salts. It has to be noted that the salts of the peptides according to the present description differ substantially from the peptides in their state(s) in vivo, as the peptides are not salts in vivo.

The term "peptide" shall also include "oligopeptide". The term "oligopeptide" is used herein to designate a series of amino acid residues, connected one to the other typically by peptide bonds between the alpha-amino and carbonyl groups of the adjacent amino acids. The length of the oligopeptide is not critical to the description, as long as the correct epitope or epitopes are maintained therein. The oligopeptides are typically less than about 30 amino acid residues in length, and greater than about 15 amino acids in length.

The term "polypeptide" designates a series of amino acid residues, connected one to the other typically by peptide bonds between the alpha-amino and carbonyl groups of the adjacent amino acids. The length of the polypeptide is not critical to the description as long as the correct epitopes are maintained. In contrast to the terms peptide or oligopeptide, the term polypeptide is meant to refer to molecules containing more than about 30 amino acid residues.

A peptide, oligopeptide, protein or polynucleotide coding for such a molecule is "immunogenic" (and thus is an "immunogen" within the present description), if it is capable of inducing an immune response. In the case of the present description, immunogenicity is more specifically defined as the ability to induce a T-cell response. Thus, an "immunogen" would be a molecule that is capable of inducing an immune response, and in the case of the present description, a molecule capable of inducing a T-cell response. In another aspect, the immunogen can be the peptide, the complex of the peptide with MHC, oligopeptide, and/or protein that is used to raise specific antibodies or TCRs against it.

A class I T-cell "epitope" requires a short peptide that is bound to a class I MHC receptor, forming a ternary complex (MHC class I alpha chain, beta-2-microglobulin, and peptide) that can be recognized by a T-cell bearing a matching T-cell receptor binding to the MHC/peptide complex with appropriate affinity. Peptides binding to MHC class I molecules are typically 8-14 amino acids in length, and most typically 9 amino acids in length.

The nucleotide sequence coding for a particular peptide, oligopeptide, or polypeptide may be naturally occurring or they may be synthetically constructed. Generally, DNA segments encoding the peptides, polypeptides, and proteins of this description are assembled from cDNA fragments and short oligonucleotide linkers, or from a series of oligonucleotides, to provide a synthetic gene that is capable of being expressed in a recombinant transcriptional unit comprising regulatory elements derived from a microbial or viral operon.

As used herein the term "a nucleotide coding for (or encoding) a peptide" refers to a nucleotide sequence coding for the peptide including artificial (man-made) start and stop codons compatible for the biological system the sequence is to be expressed by, for example, a dendritic cell or another cell system useful for the production of TCRs.

As used herein the term "a nucleotide coding for (or encoding) a TCR" refers to one or more nucleotide sequences coding for the TCR including artificial (man-made) start and stop codons compatible for the biological system the sequence is to be expressed by, for example, T-cell or another cell system useful for the production of TCRs.

As used herein, reference to a nucleic acid sequence includes both single stranded and double stranded nucleic acid. Thus, for example for DNA, the specific sequence, unless the context indicates otherwise, refers to the single strand DNA of such sequence, the duplex of such sequence with its complement (double stranded DNA) and the complement of such sequence.

The term "coding region" refers to that portion of a gene which either naturally or normally codes for the expression product of that gene in its natural genomic environment, i.e., the region coding in vivo for the native expression product of the gene.

The coding region can be derived from a non-mutated ("normal"), mutated or altered gene, or can even be derived from a DNA sequence, or gene, wholly synthesized in the laboratory using methods well known to those of skill in the art of DNA synthesis.

The term "expression product" means the polypeptide or protein that is the natural translation product of the gene and any nucleic acid sequence coding equivalents resulting from genetic code degeneracy and thus coding for the same amino acid(s).

The term "fragment", when referring to a coding sequence, means a portion of DNA comprising less than the complete coding region, whose expression product retains essentially the same biological function or activity as the expression product of the complete coding region.

The term "DNA segment" refers to a DNA polymer, in the form of a separate fragment or as a component of a larger DNA construct, which has been derived from DNA isolated at least once in substantially pure form, i.e., free of contaminating endogenous materials and in a quantity or concentration enabling identification, manipulation, and recovery of the segment and its component nucleotide sequences by standard biochemical methods, for example, by using a cloning vector. Such segments are provided in the form of an open reading frame uninterrupted by internal non-translated sequences, or introns, which are typically present in eukaryotic genes. Sequences of non-translated DNA may be present downstream from the open reading frame, where the same do not interfere with manipulation or expression of the coding regions.

The term "primer" means a short nucleic acid sequence that can be paired with one strand of DNA and provides a free 3'-OH end at which a DNA polymerase starts synthesis of a deoxyribonucleotide chain.

The term "promoter" means a region of DNA involved in binding of RNA polymerase to initiate transcription.

The term "isolated" means that the material is removed from its original environment (e.g., the natural environment, if it is naturally occurring). For example, a naturally-occurring polynucleotide or polypeptide present in a living animal is not isolated, but the same polynucleotide or polypeptide, separated from some or all of the coexisting materials in the natural system, is isolated. In an aspect, such polynucleotides are part of a vector and/or such polynucleotides or polypeptides are part of a composition, and still are isolated in that such vector or composition is not part of its natural environment.

The polynucleotides, and recombinant or immunogenic polypeptides, disclosed in accordance with the present description may also be in "purified" form. The term "purified" does not require absolute purity; rather, it is intended as a relative definition, and can include preparations that are highly purified or preparations that are only partially purified, as those terms are understood by those of skill in the relevant art. For example, individual clones isolated from a cDNA library have been conventionally purified to electrophoretic homogeneity. Purification of starting material or natural material to at least one order of magnitude, preferably two or three orders, and more preferably four or five orders of magnitude is expressly contemplated. Furthermore, a claimed polypeptide which has a purity of preferably 99.999%, or at least 99.99% or 99.9%; and even desirably 99% by weight or greater is expressly encompassed.

The nucleic acids and polypeptide expression products disclosed according to the present description, as well as expression vectors containing such nucleic acids and/or such polypeptides, may be in "enriched form". As used herein, the term "enriched" means that the concentration of the material is at least about 2, 5, 10, 100, or 1000 times its natural concentration (for example), advantageously 0.01%, by weight, preferably at least about 0.1% by weight. Enriched preparations of about 0.5%, 1%, 5%, 10%, and 20% by weight are also contemplated. The sequences, constructs, vectors, clones, and other materials comprising the present description can advantageously be in enriched or isolated form. The term "active fragment" means a fragment, usually of a peptide, polypeptide or nucleic acid sequence, that generates an immune response (i.e., has immunogenic activity) when administered, alone or optionally with a suitable adjuvant or in a vector, to an animal, such as a mammal, for example, a rabbit or a mouse, and also including a human, such immune response taking the form of stimulating a T-cell response within the recipient animal, such as a human. Alternatively, the "active fragment" may also be used to induce a T-cell response in vitro.

As used herein, the terms "portion", "segment" and "fragment", when used in relation to polypeptides, refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide. When used in relation to polynucleotides, these terms refer to the products produced by treatment of said polynucleotides with any of the endonucleases.

In accordance with the present description, the term "percent identity" or "percent identical", when referring to a sequence, means that a sequence is compared to a claimed or described sequence after alignment of the sequence to be compared (the "Compared Sequence") with the described or claimed sequence (the "Reference Sequence"). The percent identity is then determined according to the following formula:

percent identity=100[1−(C/R)]

wherein C is the number of differences between the Reference Sequence and the Compared Sequence over the length of alignment between the Reference Sequence and the Compared Sequence, wherein (i) each base or amino acid in the Reference Sequence that does not have a corresponding aligned base or amino acid in the Compared Sequence and
(ii) each gap in the Reference Sequence and
(iii) each aligned base or amino acid in the Reference Sequence that is different from an aligned base or amino acid in the Compared Sequence, constitutes a difference and
(iv) the alignment has to start at position 1 of the aligned sequences;

and R is the number of bases or amino acids in the Reference Sequence over the length of the alignment with the Compared Sequence with any gap created in the Reference Sequence also being counted as a base or amino acid.

If an alignment exists between the Compared Sequence and the Reference Sequence for which the percent identity as calculated above is about equal to or greater than a specified minimum Percent Identity then the Compared Sequence has the specified minimum percent identity to the Reference Sequence even though alignments may exist in which the herein above calculated percent identity is less than the specified percent identity.

In the description, the term "homologous" refers to the degree of identity (see percent identity above) between sequences of two amino acid sequences, i.e., peptide or polypeptide sequences. The aforementioned "homology" is determined by comparing two sequences aligned under optimal conditions over the sequences to be compared. Such a sequence homology can be calculated by creating an alignment using, for example, the ClustalW algorithm. Commonly available sequence analysis software, more specifically, Vector NTI, GENETYX or other tools are provided by public databases.

A person skilled in the art will be able to assess, whether T-cells induced by a variant of a specific peptide will be able to cross-react with the peptide itself.

By a "variant" of the given amino acid sequence the inventors mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide having the amino acid sequence of SEQ ID NO:1. For example, a peptide may be modified so that it at least maintains, if not improves, the ability to interact with and bind to the binding groove of a suitable MHC molecule, such as HLA-A*02 or -DR, and in that way it at least maintains, if not improves, the ability to bind to the TCR of activated T-lymphocytes. Similarly, a TCR may be modified so that it at least maintains, if not improves, the ability to interact with and bind to a suitable MHC molecule/KIQEILTQV (SEQ ID NO:1) complex, such as HLA-A*02 or -DR, and in that way it at least maintains, if not improves, the ability to activate T-cells.

These T-cells can subsequently cross-react with cells and kill cells that express a polypeptide that contains the natural amino acid sequence of the cognate peptide, such as KIQEILTQV (SEQ ID NO:1), as defined in the aspects of the description. As can be derived from the scientific literature and databases (Rammensee et al., 1999), certain positions of HLA binding peptides are typically anchor residues forming a core sequence fitting to the binding motif of the HLA receptor, which is defined by polar, electrophysical, hydrophobic and spatial properties of the polypeptide chains constituting the binding groove. In an aspect, one skilled in the art would have the ability given the teachings of the description to modify the amino acid sequence of a TCR, by maintaining the known anchor residues, and would be able to determine whether such TCR variants maintain the ability to bind MHC class I or II molecules/KIQEILTQV (SEQ ID NO:1) complexes. The TCR variants of the description retain the ability to bind MHC class I or II molecules/KIQEILTQV (SEQ ID NO:1) complexes. T-cells expressing the TCR variants of the description can subsequently kill cells that express a polypeptide containing the natural amino acid sequence of the cognate peptide, such as KIQEILTQV (SEQ ID NO:1).

In an aspect, the peptides or TCRs disclosed herein can be modified by the substitution of one or more residues at different, possibly selective, sites within the peptide chain, if not otherwise stated. Preferably those substitutions are located at the end of the amino acid chain of said peptide. For TCRs, preferably those substitutions are located at variable domains of TCR alpha chain and TCR beta chain. Such substitutions may be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these are often show correlation with similarities in size, charge, polarity, and hydrophobicity between the original amino acid and its replacement, and such is the basis for defining "conservative substitutions."

Conservative substitutions are herein defined as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 5—large, aromatic residues (Phe, Tyr, Trp).

Less conservative substitutions might involve the replacement of one amino acid by another that has similar characteristics but is somewhat different in size, such as replacement of an alanine by an isoleucine residue. Highly non-conservative replacements might involve substituting an acidic amino acid for one that is polar, or even for one that is basic in character. Such "radical" substitutions cannot, however, be dismissed as potentially ineffective since chemical effects are not totally predictable and radical substitutions might well give rise to serendipitous effects not otherwise predictable from simple chemical principles.

In an aspect, such substitutions may involve structures other than the common L-amino acids. Thus, D-amino acids might be substituted for the L-amino acids commonly found in the antigenic peptides of the description and yet still be encompassed by the disclosure herein.

In addition, non-standard amino acids (i.e., other than the common naturally occurring proteinogenic amino acids) may also be used for substitution purposes to produce immunogens and immunogenic polypeptides according to the present description.

If substitutions at more than one position are found to result in a peptide with substantially equivalent or greater antigenic activity as defined below, then combinations of those substitutions will be tested to determine if the combined substitutions result in additive or synergistic effects on the antigenicity of the peptide. At most, no more than 4 positions within the peptide would be simultaneously substituted.

T-Cell Receptors (TCRs)

In a preferred embodiment, the description relates a TCR comprising a TCR alpha chain shown in Table 1, and variants thereof; and a TCR beta chain shown in Table 1, and variants thereof. In an aspect, a TCR described herein has the ability to bind or specifically bind to a molecule of the human major histocompatibility complex (MHC) class-I/KIQEILTQV (SEQ ID NO:1) complex or to class II/KIQEILTQV (SEQ ID NO:1) complex.

TABLE 1

Representative TCR according to the present description

| TCR ID | Description | Sequence |
|---|---|---|
| R10P1A7 alpha chain | alpha chain | MKTFAGFSFLFLWLQLDCMSRGEDVEQSLFLSVREGD SSVINCTYTDSSSTYLYWYKQEPGAGLQLLTYIFSNMD MKQDQRLTVLLNKKDKHLSLRIADTQTGDSAIYFCAESK ETRLMFGDGTQLVVKPNIQNPDPAVYQLRDSKSSDKSV CLFTDFDSQTNVSQSKDSDVYITDKTVLDMRSMDFKSN SAVAWSNKSDFACANAFNNSIIPEDTFFPSPESSCDVKL VEKSFETDTNLNFQNLSVIGFRILLLKVAGFNLLMTLRLW SS (SEQ ID NO: 2) |
| | L segment (TRAV5) | MKTFAGFSFLFLWLQLDCMSR (SEQ ID NO: 3) |
| | V chain (TRAV5) | MKTFAGFSFLFLWLQLDCMSRGEDVEQSLFLSVREGD SSVINCTYTDSSSTYLYWYKQEPGAGLQLLTYIFSNMD MKQDQRLTVLLNKKDKHLSLRIADTQTGDSAIYFCAES (SEQ ID NO:4) |
| | CDR1 | DSSSTY (SEQ ID NO: 5) |
| | CDR2 | IFS (SEQ ID NO: 6) |
| | CDR3 | CAESKETRLMF (SEQ ID NO: 7) |
| | J segment (TRAJ31) | RLMFGDGTQLVVKP (SEQ ID NO: 8) |
| | Constant region (TRAC) | NIQNPDPAVYQLRDSKSSDKSVCLFTDFDSQTNVSQSK DSDVYITDKTVLDMRSMDFKSNSAVAWSNKSDFACAN AFNNSIIPEDTFFPSPESSCDVKLVEKSFETDTNLNFQN LSVIGFRILLLKVAGFNLLMTLRLWSS (SEQ ID NO: 9) |

TABLE 1-continued

Representative TCR according to the present description

| TCR ID | Description | Sequence |
|---|---|---|
| R10P1A7 beta chain | beta chain | MLLLLLLLGPGISLLLPGSLAGSGLGAVVSQHPSWVICK SGTSVKIECRSLDFQATTMFWYRQFPKQSLMLMATSN EGSKATYEQGVEKDKFLINHASLTLSTLTVTSAHPEDSS FYICSARAGGHEQFFGPGTRLTVLEDLKNVFPPEVAVF EPSEAEISHTQKATLVCLATGFYPDHVELSWWVNGKEV HSGVSTDPQPLKEQPALNDSRYCLSSRLRVSATFWQN PRNHFRCQVQFYGLSENDEVVTQDRAKPVTQIVSAEAW GRADCGFTSESYQQGVLSATILYEILLGKATLYAVLVSA LVLMAMVKRKDSRG (SEQ ID NO: 10) |
| | L segment (TRBV20-1) | MLLLLLLLGPGISLLLPGSLAGSGL (SEQ ID NO: 11) |
| | V chain (TRBV20-1 ) | MLLLLLLLGPGISLLLPGSLAGSGLGAVVSQHPSWVICK SGTSVKIECRSLDFQATTMFWYRQFPKQSLMLMATSN EGSKATYEQGVEKDKFLINHASLTLSTLTVTSAHPEDSS FYICSAR (SEQ ID NO: 12) |
| | CDR1 | DFQATT (SEQ ID NO: 13) |
| | CDR2 | SNEGSKA (SEQ ID NO: 14) |
| | CDR3 | CSARAGGHEQFF (SEQ ID NO: 15) |
| | J chain (TRBJ2-1) | EQFFGPGTRLTVL (SEQ ID NO: 16) |
| | constant region (TRBC2) | EDLKNVFPPEVAVFEPSEAEISHTQKATLVCLATGFYPD HVELSWWVNGKEVHSGVSTDPQPLKEQPALNDSRYCL SSRLRVSATFWQNPRNHFRCQVQFYGLSENDEVVTQD RAKPVTQIVSAEAWGRADCGFTSESYQQGVLSATILYEI LLGKATLYAVLVSALVLMAMVKRKDSRG (SEQ ID NO: 17) |

The alpha and beta chains of alpha/beta TCR's, and the gamma and delta chains of gamma/delta TCRs, are generally regarded as each having two "domains", namely variable and constant domains. The variable domain consists of a concatenation of variable region (V), and joining region (J). The variable domain may also include a leader region (L). Beta and delta chains may also include a diversity region (D). The alpha and beta constant domains may also include C-terminal transmembrane (TM) domains that anchor the alpha and beta chains to the cell membrane.

In the present description, the term "TCR alpha variable domain" therefore refers to the concatenation of the TCR alpha V (TRAV) region without leader region (L), and the TCR alpha J (TRAJ) region, and the term "TCR alpha constant domain" refers to the extracellular TRAC region, or to a C-terminal truncated TRAC sequence, and optionally an alpha transmembrane domain (VIGFRILLLKVAGFN-LLMTL (SEQ ID NO:18)).

Likewise the term "TCR beta variable domain" refers to the concatenation of the TCR beta V (TRBV) region without leader region (L) and the TCR beta D/J (TRBD/TRBJ) region, and the term "TCR beta constant domain" refers to the extracellular TRBC region, or to a C-terminal truncated TRBC sequence, and optionally a beta transmembrane domain (TILYEILLGKATLYAVLVSALVL (SEQ ID NO:19)).

With respect to gamma/delta TCRs, the term "TCR gamma variable domain" as used herein refers to the concatenation of the TCR gamma V (TRGV) region without leader region (L), and the TCR gamma J (TRGJ) region, and the term TCR gamma constant domain refers to the extracellular TRGC region, or to a C-terminal truncated TRGC sequence. Likewise the term "TCR delta variable domain" refers to the concatenation of the TCR delta V (TRDV) region without leader region (L) and the TCR delta D/J (TRDD/TRDJ) region, and the term "TCR delta constant domain" refers to the extracellular TRDC region, or to a C-terminal truncated TRDC sequence.

In an embodiment, a TCR of the present description comprises or consists of a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to a TCR alpha chain shown in Table 1. The TCR alpha chains shown in Table 1 contain a leader (L) segment; a V chain; three complimentary determining regions (CDR1, CDR2 and CDR3); a joining region (J) and a constant region, as defined in Table 1.

In an embodiment, a TCR of the present description comprises or consists of a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to a TCR alpha variable domain shown in Table 1.

In an embodiment, a TCR of the present description comprises or consists of, a TCR alpha constant domain at least 75%, 80%, 90%, 91%, 92%, 93%, 94%, 95%, 96%, 97%, 98%, or 99% identical, preferably 75% identical, to a TCR alpha constant domain shown in Table 1.

In an embodiment, a TCR of the present description comprises, or consists of, a TCR alpha variable domain comprising at least one alpha chain complementarity determining region (CDR) selected from the group consisting of an alpha chain CDR1, CDR2 and CDR3 shown in Table 1. In a preferred embodiment, the TCR alpha variable domain comprises an alpha chain CDR3 shown in Table 1. In another preferred embodiment, the TCR alpha variable domain comprises an alpha chain CDR1, CDR2 and CDR3 shown in Table 1.

In a particularly preferred embodiment, a TCR of the present description comprises, or consists of, a TCR alpha variable domain having at least 90% sequence identity to a TCR alpha variable domain of Table 1, and comprises CDR1, CDR2 and CDR3 of the same alpha variable domain of Table 1.

In an embodiment, a TCR of the present description comprises, or consists of, a TCR beta chain at least 75%, 80%, 90%, 91%, 92%, 93%, 94%, 95%, 96%, 97%, 98%, or 99% identical, preferably 90%, 95%, 96%, 97%, 98%, or 99% identical, to a TCR beta chain shown in Table 1. The TCR beta chains shown in Table 1 contain a leader (L) segment; a V chain; three complimentary determining regions (CDR1, CDR2 and CDR3); a joining region (J) and a constant region, as defined in Table 1.

In an embodiment, a TCR of the present description comprises, or consists of, a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to a TCR beta variable domain shown in Table 1.

In an embodiment, a TCR of the present description comprises, or consists of, a TCR beta constant domain at least 75%, 80%, 90%, 91%, 92%, 93%, 94%, 95%, 96%, 97%, 98%, or 99% identical, preferably 75% identical, to a TCR beta constant domain shown in Table 1.

In an embodiment, a TCR of the present description comprises, or consists of, a TCR beta variable domain comprising at least one beta chain complementarity determining region (CDR) selected from the group consisting of a beta chain CDR1, CDR2 and CDR3 shown in Table 1. In a preferred embodiment, the TCR beta variable domain comprises a beta chain CDR3 shown in Table 1. In another preferred embodiment, the TCR beta variable domain comprises a beta chain CDR1, CDR2 and CDR3 shown in Table 1.

In a particularly preferred embodiment, a TCR of the present description comprises, or consists of, a TCR beta variable domain having at least 90% or 95% sequence identity to a TCR beta variable domain of Table 1, and comprises CDR1, CDR2 and CDR3 of the same TCR beta variable domain of Table 1.

The alpha chain variable domain may comprise one or more alpha CDR domains having one, two, three or four amino acid substitutions relative to the corresponding CDR sequence shown in Table 1. Likewise, the beta chain variable domain may comprise one or more beta CDR domains having one, two, three or four amino acid substitutions relative to the corresponding beta CDR sequence shown in Table 1.

The TCR alpha chain and TCR beta chain may be fused to form a single chain TCR. Alternatively, the TCR alpha and beta chains may be expressed as separate proteins which can be assembled into a heterodimer.

In one embodiment, any TCR alpha chain of Table 1 is paired with any other TCR beta chain to produce a TCR that specifically binds to an IGF2BP3-001 peptide-HLA molecule complex. In another embodiment, any TCR beta chain of Table 1 is paired with any other TCR alpha chain to produce a TCR that specifically binds to an IGF2BP3-001 peptide-HLA molecule complex.

TCR R10P1A7

In one embodiment, a TCR of the present description comprises, or consists of, the alpha chain and/or beta chain of TCR R10P1A7, corresponding to SEQ ID NO:2 and SEQ ID NO:10, respectively.

The TCR alpha variable domain of TCR R10P1A7 comprises, or alternatively consists of, amino acids 22 to 130 of SEQ ID NO:2; the TCR alpha constant domain of TCR R10P1A7 comprises, or alternatively consists of, amino acids 131 to 271 of SEQ ID NO:2; the TCR beta variable domain of TCR R10P1A7 comprises, or alternatively consists of, amino acids 26 to 139 of SEQ ID NO:10; and the TCR beta constant domain comprises, or alternatively consists of, amino acids 140 to 318 of SEQ ID NO:10.

In a particular embodiment, a TCR of the present description comprises a TCR alpha chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha chain of SEQ ID NO:2.

In another embodiment, a TCR of the present description comprises a TCR alpha variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR alpha variable domain of SEQ ID NO:2.

In an embodiment, a TCR of the present description comprises a TCR alpha constant domain at least 75%, 80%, 90%, 91%, 92%, 93%, 94%, 95%, 96%, 97%, 98%, or 99% identical, preferably 75% identical, to the TCR alpha constant domain of SEQ ID NO:2.

In an embodiment, a TCR of the present description comprises a TCR alpha variable domain comprising at least one alpha chain complementarity determining region (CDR) selected from the group consisting of the alpha chain CDR1, CDR2 and CDR3 of SEQ ID NO:2. In a preferred embodiment, the TCR alpha variable domain comprises the alpha chain CDR3 of SEQ ID NO:2. In another preferred embodiment, the TCR alpha variable domain comprises the alpha chain CDR1, CDR2 and CDR3 of SEQ ID NO:2.

In a particularly preferred embodiment, a TCR of the present description comprises a TCR alpha variable domain having at least 90% sequence identity to the TCR alpha variable domain of SEQ ID NO:2, and comprises the CDR1, CDR2 and CDR3 of SEQ ID NO:2.

In another particular embodiment, a TCR of the present description comprises a TCR beta chain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta chain of SEQ ID NO:10.

In an embodiment, a TCR of the present description comprises a TCR beta variable domain at least 75%, 80%, 90%, 91%, 92%, 93%, 94%, 95%, 96%, 97%, 98%, or 99% identical, preferably 90%, 95%, 96%, 97%, 98%, or 99% identical, to the TCR beta variable domain of SEQ ID NO:10.

In an embodiment, a TCR of the present description comprises a TCR beta constant domain at least 75%, 80%, 90%, 91%, 92%, 93%, 94%, 95%, 96%, 97%, 98%, or 99% identical, preferably 75% identical, to the TCR beta constant domain of SEQ ID NO:10.

In an embodiment, a TCR of the present description comprises a TCR beta variable domain comprising at least one beta chain complementarity determining region (CDR) selected from the group consisting of the beta chain CDR1, CDR2 and CDR3 of SEQ ID NO:10. In a preferred embodiment, the TCR beta variable domain comprises the beta chain CDR3 of SEQ ID NO:10. In another preferred embodiment, the TCR beta variable domain comprises the beta chain CDR1, CDR2 and CDR3 of SEQ ID NO:10.

In a particularly preferred embodiment, a TCR of the present description comprises a TCR beta variable domain having at least 90% sequence identity to the TCR beta variable domain of SEQ ID NO:10, and comprises CDR1, CDR2 and CDR3 of SEQ ID NO:10.

The alpha chain variable domain may comprise one or more alpha CDR domains having one, two, three or four amino acid substitutions relative to the corresponding CDR sequence of SEQ ID NO:2. Likewise, the beta chain variable domain may comprise one or more beta CDR domains having one, two, three or four amino acid substitutions relative to the corresponding beta CDR sequence of SEQ ID NO:10.

In a further preferred embodiment, a TCR of the present description specifically binds to an IGF2BP3 peptide-HLA molecule complex, wherein the IGF2BP3 peptide is selected from KIQEILTQV (SEQ ID NO:1) and variants thereof. In an embodiment the HLA molecule is a class I MHC molecule selected from the group consisting of HLA-A, HLA-B, and HLA-C molecules. In one embodiment the HLA molecule is HLA-A*02. In another embodiment, the HLA molecule is a class II MHC molecule selected from the group consisting of HLA-DP, HLA-DQ, and HLA-DR.

TCRs of the present description preferably bind to an IGF2BP3 peptide-HLA molecule complex with a binding affinity ($K_D$) of about 100 µM or less, about 50 µM or less, about 25 µM or less, or about 10 µM or less. More preferred are high affinity TCRs having binding affinities of about 1 µM or less, about 100 nM or less, about 50 nM or less, about 25 nM or less. Nonlimiting examples of preferred binding affinity ranges for TCRs of the present invention include about 1 nM to about 10 nM; about 10 nM to about 20 nM; about 20 nM to about 30 nM; about 30 nM to about 40 nM; about 40 nM to about 50 nM; about 50 nM to about 60 nM; about 60 nM to about 70 nM; about 70 nM to about 80 nM; about 80 nM to about 90 nM; and about 90 nM to about 100 nM.

As used herein in connect with TCRs of the present description, "specific binding" and grammatical variants thereof are used to mean a TCR having a binding affinity ($K_D$) for an IGF2BP3 peptide-HLA molecule complex of 100 µM or less.

Alpha/beta heterodimeric TCRs of the present description may have an introduced disulfide bond between their constant domains. Preferred TCRs of this type include those which have a TRAC constant domain sequence and a TRBC1 or TRBC2 constant domain sequence except that Thr 48 of TRAC and Ser 57 of TRBC1 or TRBC2 are replaced by cysteine residues, the said cysteines forming a disulfide bond between the TRAC constant domain sequence and the TRBC1 or TRBC2 constant domain sequence of the TCR.

With or without the introduced inter-chain bond mentioned above, alpha/beta heterodimeric TCRs of the present description may have a TRAC constant domain sequence and a TRBC1 or TRBC2 constant domain sequence, and the TRAC constant domain sequence and the TRBC1 or TRBC2 constant domain sequence of the TCR may be linked by the native disulfide bond between Cys4 of exon 2 of TRAC and Cys2 of exon 2 of TRBC1 or TRBC2.

TCRs of the present description may comprise a detectable label selected from the group consisting of a radionuclide, a fluorophore and biotin. TCRs of the present description may be conjugated to a therapeutically active agent, such as a radionuclide, a chemotherapeutic agent, or a toxin.

In an embodiment, a TCR of the present description having at least one mutation in the alpha chain and/or having at least one mutation in the beta chain has modified glycosylation compared to the unmutated TCR.

In an embodiment, a TCR comprising at least one mutation in the TCR alpha chain and/or TCR beta chain has a binding affinity for, and/or a binding half-life for, an IGF2BP3 peptide-HLA molecule complex, which is at least double that of a TCR comprising the unmutated TCR alpha chain and/or unmutated TCR beta chain. Affinity-enhancement of tumor-specific TCRs, and its exploitation, relies on the existence of a window for optimal TCR affinities. The existence of such a window is based on observations that TCRs specific for HLA-A2-restricted pathogens have KD values that are generally about 10-fold lower when compared to TCRs specific for HLA-A2-restricted tumor-associated self-antigens (Aleksic et al. 2012; Kunert et al. 2013). It is now known, although tumor antigens have the potential to be immunogenic, because tumors arise from the individual's own cells only mutated proteins or proteins with altered translational processing will be seen as foreign by the immune system.

Antigens that are upregulated or overexpressed (so called self-antigens) will not necessarily induce a functional immune response against the tumor: T-cells expressing TCRs that are highly reactive to these antigens will have been negatively selected within the thymus in a process known as central tolerance (Xing et al. 2012; Ruella et al. 2014; Sharpe et al. 2015), meaning that only T-cells with low-affinity TCRs for self-antigens remain. Therefore, affinity of TCRs or variants of the present description to IGF2BP3 can be enhanced by methods well known in the art.

A "pharmaceutical composition" is a composition suitable for administration to a human being in a medical setting. Preferably, a pharmaceutical composition is sterile and produced according to GMP guidelines.

Pharmaceutical compositions of the present description also include at least one host cell expressing a TCR of the present description, in a pharmaceutically acceptable carrier.

Pharmaceutical compositions of the present description may also include pharmaceutically acceptable excipients and/or stabilizers.

This composition is used for parenteral administration, such as subcutaneous, intradermal, intramuscular or oral administration. For this, the peptides and optionally other molecules are dissolved or suspended in a pharmaceutically acceptable, preferably aqueous carrier. In addition, the composition can contain excipients, such as buffers, binding agents, blasting agents, diluents, flavors, lubricants, etc. An extensive listing of excipients that can be used in such a composition, can be, for example, taken from A. Kibbe, Handbook of Pharmaceutical Excipients (Kibbe, 2000). The composition can be used for a prevention, prophylaxis and/or therapy of adenomatous or cancerous diseases. Exemplary formulations can be found in, for example, EP2112253, which is herein incorporated by reference in its entirety.

A further aspect of the description provides nucleic acids (for example polynucleotides) encoding a peptide, peptide variants, TCRs and TCR variants of the description. The polynucleotide may be, for example, DNA, cDNA, PNA, RNA or combinations thereof, either single- and/or double-stranded, or native or stabilized forms of polynucleotides, such as, for example, polynucleotides with a phosphorothioate backbone and it may or may not contain introns so long as it codes for the peptide. Of course, only peptides that contain naturally occurring amino acid residues joined by naturally occurring peptide bonds are encodable by a polynucleotide. A still further aspect of the description provides an expression vector capable of expressing a polypeptide according to the description.

A variety of methods have been developed to link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. Synthetic linkers containing a variety of restriction endonuclease sites are commercially available from a number of sources including International Biotechnologies Inc. New Haven, Conn., USA.

A desirable method of modifying the DNA encoding the polypeptide of the description employs the polymerase chain reaction as disclosed by Saiki R K, et al. (Saiki et al., 1988). This method may be used for introducing the DNA into a suitable vector, for example by engineering in suitable restriction sites, or it may be used to modify the DNA in other useful ways as is known in the art. If viral vectors are used, pox- or adenovirus vectors are preferred.

In one aspect, to obtain T-cells expressing TCRs of the present description, nucleic acids encoding TCR-alpha and/or TCR-beta chains of the present description are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs are synthesized by techniques known in the art, e.g., in vitro transcription systems. The in vitro-synthesized TCR RNAs are then introduced into primary CD8+ T-cells obtained from healthy donors by electroporation to re-express tumor specific TCR-alpha and/or TCR-beta chains.

TCR chains introduced into a peripheral T-cell may compete with endogenous TCR chains for association with the CD3 complex, which is necessary for TCR surface expression. Because a high level of TCR surface expression is essential to confer appropriate sensitivity for triggering by cells expressing the target tumor antigen (Cooper et al., 2000; Labrecque et al., 2001), strategies that enhance TCR-alpha and TCR-beta gene expression levels are an important consideration in TCR gene therapy.

To increase the expression, nucleic acids encoding TCRs of the present description may be operably linked to strong promoters, such as retroviral long terminal repeats (LTRs), cytomegalovirus (CMV), murine stem cell virus (MSCV) U3, phosphoglycerate kinase (PGK), β-actin, ubiquitin, and a simian virus 40 (SV40)/CD43 composite promoter (Cooper et al., 2004; Jones et al., 2009), elongation factor (EF)-1a (Tsuji et al., 2005) and the spleen focus-forming virus (SFFV) promoter (Joseph et al., 2008). In a preferred embodiment, the promoter is heterologous to the nucleic acid being expressed.

In addition to strong promoters, TCR expression cassettes of the present description may contain additional elements that can enhance transgene expression, including a central polypurine tract (cPPT), which promotes the nuclear translocation of lentiviral constructs (Follenzi et al., 2000), and the woodchuck hepatitis virus posttranscriptional regulatory element (wPRE), which increases the level of transgene expression by increasing RNA stability (Zufferey et al., 1999).

The alpha and beta chains of a TCR of the present invention may be encoded by nucleic acids located in separate vectors, or may be encoded by polynucleotides located in the same vector.

Achieving high-level TCR surface expression requires that both the TCR-alpha and TCR-beta chains of the introduced TCR be transcribed at high levels. To do so, the TCR-alpha and TCR-beta chains of the present description may be cloned into bicistronic constructs in a single vector, which has been shown to be capable of overcoming this obstacle. The use of a viral intraribosomal entry site (IRES) between the TCR-alpha and TCR-beta chains results in the coordinated expression of both chains, because the TCR-alpha and TCR-beta chains are generated from a single transcript that is broken into two proteins during translation, ensuring that an equal molar ratio of TCR-alpha and TCR-beta chains are produced. (Schmitt et al. 2009).

Nucleic acids encoding TCRs of the present description may be codon optimized to increase expression from a host cell. Redundancy in the genetic code allows some amino acids to be encoded by more than one codon, but certain codons are less "optimal" than others because of the relative availability of matching tRNAs as well as other factors (Gustafsson et al., 2004). Modifying the TCR-alpha and TCR-beta gene sequences such that each amino acid is encoded by the optimal codon for mammalian gene expression, as well as eliminating mRNA instability motifs or cryptic splice sites, has been shown to significantly enhance TCR-alpha and TCR-beta gene expression (Scholten et al., 2006).

Furthermore, mispairing between the introduced and endogenous TCR chains may result in the acquisition of specificities that pose a significant risk for autoimmunity. For example, the formation of mixed TCR dimers may reduce the number of CD3 molecules available to form properly paired TCR complexes, and therefore can significantly decrease the functional avidity of the cells expressing the introduced TCR (Kuball et al., 2007).

To reduce mispairing, the C-terminus domain of the introduced TCR chains of the present description may be modified in order to promote interchain affinity, while decreasing the ability of the introduced chains to pair with the endogenous TCR. These strategies may include replacing the human TCR-alpha and TCR-beta C-terminus domains with their murine counterparts (murinized C-terminus domain); generating a second interchain disulfide bond in the C-terminus domain by introducing a second cysteine residue into both the TCR-alpha and TCR-beta chains of the introduced TCR (cysteine modification); swapping interacting residues in the TCR-alpha and TCR-beta chain C-terminus domains ("knob-in-hole"); and fusing the variable domains of the TCR-alpha and TCR-beta chains directly to CD3ζ (CD3ζ fusion). (Schmitt et al. 2009).

The DNA (or in the case of retroviral vectors, RNA) may then be expressed in a suitable host to produce a polypeptide comprising the peptide or variant of the description. Thus, the DNA encoding the peptide or variant of the description may be used in accordance with known techniques, appropriately modified in view of the teachings contained herein, to construct an expression vector, which is then used to transform an appropriate host cell for the expression and production of the polypeptide of the description. Such techniques include those disclosed, for example, in U.S. Pat. Nos. 4,440,859, 4,530,901, 4,582,800, 4,677,063, 4,678, 751, 4,704,362, 4,710,463, 4,757,006, 4,766,075, and 4,810, 648, which are herein incorporated by reference.

The DNA (or in the case of retroviral vectors, RNA) encoding the polypeptide constituting the compound of the description may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance.

Alternatively, the gene for such selectable trait can be on another vector, which is used to co-transform the desired host cell.

Host cells that have been transformed by the recombinant DNA of the description are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus* spec.), plant-cells, animal cells and insect-cells. Preferably, the system can be mammalian cells such as CHO cells available from the ATCC Cell Biology Collection.

In an embodiment, a host cell is engineered to express a TCR of the present description. In preferred embodiments, the host cell is a human T-cell or T-cell progenitor. In some embodiments the T-cell or T-cell progenitor is obtained from a cancer patient. In other embodiments the T-cell or T-cell progenitor is obtained from a healthy donor. Host cells of the present description can be allogeneic or autologous with respect to a patient to be treated. In one embodiment, the host is a gamma/delta T-cell transformed to express an alpha/beta TCR.

A typical mammalian cell vector plasmid for constitutive expression comprises the CMV or SV40 promoter with a suitable poly A tail and a resistance marker, such as neomycin. One example is pSVL available from Pharmacia, Piscataway, N.J., USA. An example of an inducible mammalian expression vector is pMSG, also available from Pharmacia. Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps). CMV promoter-based vectors (for example from Sigma-Aldrich) provide transient or stable expression, cytoplasmic expression or secretion, and N-terminal or C-terminal tagging in various combinations of FLAG, 3×FLAG, c-myc or MAT. These fusion proteins allow for detection, purification and analysis of recombinant protein. Dual-tagged fusions provide flexibility in detection.

The strong human cytomegalovirus (CMV) promoter regulatory region drives constitutive protein expression levels as high as 1 mg/L in COS cells. For less potent-cell lines, protein levels are typically ~0.1 mg/L. The presence of the SV40 replication origin will result in high levels of DNA replication in SV40 replication permissive COS cells. CMV vectors, for example, can contain the pMB1 (derivative of pBR322) origin for replication in bacterial cells, the b-lactamase gene for ampicillin resistance selection in bacteria, hGH polyA, and the f1 origin. Vectors containing the pre-pro-trypsin leader (PPT) sequence can direct the secretion of FLAG fusion proteins into the culture medium for purification using ANTI-FLAG antibodies, resins, and plates. Other vectors and expression systems are well known in the art for use with a variety of host cells.

In another embodiment two or more peptides or peptide variants of the description are encoded and thus expressed in a successive order (similar to "beads on a string" constructs). In doing so, the peptides or peptide variants may be linked or fused together by stretches of linker amino acids, such as for example LLLLLL, or may be linked without any additional peptide(s) between them. These constructs can also be used for cancer therapy, and may induce immune responses both involving MHC I and MHC II.

The present description also relates to a host cell transformed with a polynucleotide vector construct of the present description. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and colon cell lines. Yeast host cells include YPH499, YPH500 and YPH501, which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect-cells are Sf9 cells which can be transfected with baculovirus expression vectors. An overview regarding the choice of suitable host cells for expression can be found in, for example, the textbook of Paulina Balbás and Argelia Lorence "Methods in Molecular Biology Recombinant Gene Expression, Reviews and Protocols," Part One, Second Edition, ISBN 978-1-58829-262-9, and other literature known to the person of skill.

Transformation of appropriate cell hosts with a DNA construct of the present description is accomplished by well-known methods that typically depend on the type of vector used. With regard to transformation of prokaryotic host cells, see, for example, Cohen et al. (Cohen et al., 1972) and (Green and Sambrook, 2012). Transformation of yeastcells is described in Sherman et al. (Sherman et al., 1986). The method of Beggs (Beggs, 1978) is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA. Electroporation is also useful for transforming and/or transfecting cells and is well known in the art for transforming yeast-cell, bacterial cells, insect-cells and vertebrate cells.

Successfully transformed cells, i.e., cells that contain a DNA construct of the present description, can be identified by well-known techniques such as PCR. Alternatively, the presence of the protein in the supernatant can be detected using antibodies.

It will be appreciated that certain host cells of the description are useful in the preparation of the peptides of the description, for example bacterial, yeast and insect-cells. However, other host cells may be useful in certain therapeutic methods. For example, antigen-presenting cells, such as dendritic cells, may usefully be used to express the peptides of the description such that they may be loaded into appropriate MHC molecules. Thus, the current description provides a host cell comprising a nucleic acid or an expression vector according to the description.

In a preferred embodiment the host cell is an antigen presenting cell, in particular a dendritic cell or antigen presenting cell. APCs loaded with a recombinant fusion protein containing prostatic acid phosphatase (PAP) were approved by the U.S. Food and Drug Administration (FDA) on Apr. 29, 2010, to treat asymptomatic or minimally symptomatic metastatic HRPC (Sipuleucel-T) (Rini et al., 2006; Small et al., 2006).

A further aspect of the description provides a method of producing a peptide or its variant, the method comprising culturing a host cell and isolating the peptide from the host cell or its culture medium.

In another embodiment the TCRs, the nucleic acid or the expression vector of the description are used in medicine. For example, the peptide or its variant may be prepared for intravenous (i.v.) injection, sub-cutaneous (s.c.) injection, intradermal (i.d.) injection, intraperitoneal (i.p.) injection, intramuscular (i.m.) injection. Preferred methods of peptide injection include s.c., i.d., i.p., i.m., and i.v. Preferred methods of DNA injection include i.d., i.m., s.c., i.p. and i.v. Doses of e.g., between 50 µg and 1.5 mg, preferably 125 µg to 500 µg, of peptide or DNA may be given and will depend on the respective peptide or DNA. Dosages of this range were successfully used in previous trials (Walter et al., 2012).

The polynucleotide used for active vaccination may be substantially pure, or contained in a suitable vector or delivery system. The nucleic acid may be DNA, cDNA, PNA, RNA or a combination thereof. Methods for designing and introducing such a nucleic acid are well known in the art. An overview is provided by e.g., Teufel et al. (Teufel et al., 2005). Polynucleotide vaccines are easy to prepare, but the mode of action of these vectors in inducing an immune response is not fully understood. Suitable vectors and delivery systems include viral DNA and/or RNA, such as systems based on adenovirus, vaccinia virus, retroviruses, herpes virus, adeno-associated virus or hybrids containing elements of more than one virus. Nonviral delivery systems include cationic lipids and cationic polymers and are well known in the art of DNA delivery. Physical delivery, such as via a "gene-gun" may also be used. The peptide or peptides encoded by the nucleic acid may be a fusion protein, for example with an epitope that stimulates T-cells for the respective opposite CDR as noted above.

The present description further relates to aptamers. Aptamers (see for example WO 2014/191359 and the literature as cited therein) are short single-stranded nucleic acid molecules, which can fold into defined three-dimensional structures and recognize specific target structures. They have appeared to be suitable alternatives for developing targeted therapies. Aptamers have been shown to selectively bind to a variety of complex targets with high affinity and specificity.

Aptamers recognizing cell surface located molecules have been identified within the past decade and provide means for developing diagnostic and therapeutic approaches. Since aptamers have been shown to possess almost no toxicity and immunogenicity they are promising candidates for biomedical applications. Indeed aptamers, for example prostate-specific membrane-antigen recognizing aptamers, have been successfully employed for targeted therapies and shown to be functional in xenograft in vivo models. Furthermore, aptamers recognizing specific tumor cell lines have been identified.

DNA aptamers can be selected to reveal broad-spectrum recognition properties for various cancer cells, and particularly those derived from solid tumors, while non-tumorigenic and primary healthy cells are not recognized. If the identified aptamers recognize not only a specific tumor sub-type but rather interact with a series of tumors, this renders the aptamers applicable as so-called broad-spectrum diagnostics and therapeutics.

Further, investigation of cell-binding behavior with flow cytometry showed that the aptamers revealed very good apparent affinities that are within the nanomolar range.

Aptamers are useful for diagnostic and therapeutic purposes. In an aspect, at least one or more aptamers are taken up by tumor cells and thus can function as molecular vehicles for the targeted delivery of anti-cancer agents such as siRNA into tumor cells.

Aptamers can be selected against complex targets such as cells and tissues and complexes of the peptides or the TCRs comprising, preferably consisting of, a sequence according to any of SEQ ID NO 14 to SEQ ID NO 15, according to the description at hand with the MHC molecule, using the cell-SELEX (Systematic Evolution of Ligands by Exponential enrichment) technique.

In one embodiment the description provides a method of producing a TCR as described herein, the method comprising culturing a host cell capable of expressing the TCR under conditions suitable to promote expression of the TCR.

The present description further relates to a method of identifying and isolating a TCR according to the present description, said method comprising incubating PBMCs from HLA-A*02-negative healthy donors with A2/IGF2BP3 monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising incubating PBMCs from HLA-A*02-negative healthy donors with A2/p286-1Y2L monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising incubating PBMCs from HLA-A*02-negative healthy donors with A2/p286-1Y2L9L monomers, incubating the PBMCs with tetramer-phycoerythrin (PE) and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with IGF2BP3-001, incubating PBMCs obtained from the transgenic mice with tetramer-phycoerythrin (PE), and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L, incubating PBMCs obtained from the transgenic mice with tetramer-phycoerythrin (PE), and isolating the high avidity T-cells by fluorescence activated cell sorting (FACS)-Calibur analysis.

The present description further relates to a method of identifying and isolating a TCR according to the present description, said method comprising obtaining a transgenic mouse with the entire human TCRαβ gene loci (1.1 and 0.7 Mb), whose T-cells express a diverse human TCR repertoire that compensates for mouse TCR deficiency, immunizing the mouse with p286-1Y2L9L, incubating PBMCs obtained from the transgenic mice with tetramer-phycoerythrin (PE), and isolating the high avidity T-cells by fluorescence activated cell sorting (FACS)-Calibur analysis.

The present description further relates to the method according to the description, wherein the T-cell comprises an expression vector capable of expressing A TCR according to the present description.

The present description further relates to a method of killing target-cells in a patient which target-cells aberrantly express IGF2BP3, the method comprising administering to the patient an effective number of TCRs, soluble TCRs and/or T-cells as according to the present description.

The present description further relates to the use of any TCR described, a nucleic acid according to the present description, an expression vector according to the present description, a cell according to the present description, or an activated cytotoxic T lymphocyte according to the present description as a medicament or in the manufacture of a medicament. The present description further relates to a use according to the present description, wherein the medicament is active against cancer.

The present description further relates to a use according to the description, wherein said cancer cells are non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

The present description further relates to a method of killing cancer cells comprising contact the cancer cells with a host cell of the present description. In one embodiment, the host cell expresses a TCR of the present description. In one embodiment the host cell is a T-cell or T-cell progenitor. In one embodiment, In a preferred embodiment the cancer cells are selected from non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer. In some embodiments, the TCR is conjugated to a therapeutically active agent. In certain embodiments the therapeutically active agent is selected from the group consisting of a radionuclide, a chemotherapeutic agent, and a toxin.

The present invention further relates to a method of treating cancer comprising administering to a subject in need thereof a host cell of the present invention. In one embodiment, the host cell expresses a TCR of the present description. In one embodiment the host cell is a T-cell or T-cell progenitor. In one embodiment the host cell is autologous to the subject to be treated. In another embodiment the host cell is allogeneic to the subject to be treated. In a preferred embodiment the cancer cells are selected from non-small cell lung cancer cells or other solid or haematological tumor cells such as non-small cell lung cancer, small cell lung cancer, renal cell cancer, brain cancer, gastric cancer, colorectal cancer, hepatocellular cancer, pancreatic cancer, prostate cancer, leukemia, breast cancer, Merkel cell carcinoma, melanoma, ovarian cancer, urinary bladder cancer, uterine cancer, gallbladder and bile duct cancer and esophageal cancer.

In some embodiments, the TCR is conjugated to a therapeutically active agent. As used herein, the term "therapeutically active agent" means a compound used to treat or prevent a disease or undesirable medical condition. In one embodiment, the therapeutically active agent is used to treat or prevent cancer. In certain embodiments the therapeutically active agent is selected from the group consisting of a radionuclide, a chemotherapeutic agent, and a toxin.

TCRs, nucleic acids and host cells of the present description, and pharmaceutical compositions thereof, may be administered to a subject in need thereof by routes known in the art, and may vary depending on the type of cancer to be treated. Routes of administration include, for example, local administration (such as intratumoral) and parenteral administration such as subcutaneous, intraperitoneal, intramuscular, intravenous, intraportal and intrahepatic. In a preferred embodiment, TCRs, nucleic acids or host cells of the present description, or pharmaceutical compositions thereof, are administered to a subject by local infusion, for example using an infusion pump and/or catheter system, to a site to be treated, such as a solid tumor. In one embodiment, a composition of the present description is infused into a solid tumor, a blood vessel that feeds a solid tumor, and/or the area surrounding a solid tumor.

In preferred embodiments, compositions of the present description are administered to a subject using a dosing regimen of at least two administrations separated by at least 24 hours. Dosing regimens suitable for administering compositions of the present description include, for example, once a day, once every two days, and once every three days. More preferred dosing regimens include once a week, twice a week, once every other week, once a month, and twice a month. In particular embodiments, a dose escalation regimen is used, wherein a series of increasing doses is administered to a subject over a period of days, weeks or months.

Effective doses of host cells expressing TCRs of the present invention include, for example at least about $10^4$, at least about $10^5$, at least about $10^6$, at least about $10^7$, at least about $10^8$, at least about $10^9$, and at least $10^{10}$ host cells per dose. In one embodiment, host cells of the present description are administered in a dose of between about $10^4$ to about $10^{10}$ cells per dose, preferably in a dose of between about $10^5$ to about $10^9$ cells per dose. In preferred embodiments, doses are administered in a dosing regimen over the course of at least two or more dosing cycles.

The present invention also relates to a method of treating cancer comprising administering a TCR, a nucleic acid, or a host cell of the present description in combination with at least one chemotherapeutic agent and/or radiation therapy.

Also provided is a method of treating cancer in a subject in need thereof, comprising:
a) isolating a cell from said subject;
b) transforming the cell with at least one vector encoding a TCR of the present description to produce a transformed cell;
c) expanding the transformed cell to produce a plurality of transformed cells; and
d) administering the plurality of transformed cells to said subject.

Also provided is a method of treating cancer in a subject in need thereof, comprising:
a) isolating a cell from a healthy donor;
b) transforming the cell with a vector encoding a TCR of the present description to produce a transformed cell;
c) expanding the transformed cell to produce a plurality of transformed cells; and
d) administering the plurality of transformed cells to said subject.

Also provided is a method of detecting cancer in a biological sample comprising:
a) contacting the biological sample with a TCR of the present description;
b) detecting binding of the TCR to the biological sample.

In some embodiments the method of detecting cancer is carried out in vitro, in vivo or in situ.

The present description further relates to particular marker proteins and biomarkers based on the peptides according to the present description, herein called "targets" that can be used in the diagnosis and/or prognosis of non-small cell lung cancer. The present description also relates to the use of these novel targets for cancer treatment.

It is a further aspect of the description to provide a method for producing a soluble T-cell receptor (sTCR) recognizing a specific peptide-MHC complex. Such soluble T-cell receptors can be generated from specific T-cell clones, and their affinity can be increased by mutagenesis targeting the complementarity-determining regions. For the purpose of T-cell receptor selection, phage display can be used (US 2010/0113300, (Liddy et al., 2012)). For the purpose of stabilization of T-cell receptors during phage display and in case of practical use as drug, alpha and beta chain can be linked e.g., by non-native disulfide bonds, other covalent bonds (single-chain T-cell receptor), or by dimerization domains (Boulter et al., 2003; Card et al., 2004; Willcox et al., 1999). The T-cell receptor can be linked to toxins, drugs, cytokines (see, for example, US 2013/0115191), or domains recruiting effector cells such as an anti-CD3 domain, etc., in order to execute particular functions on target-cells. In another aspect, it is expressed in T-cells used for adoptive transfer. See, for example, WO 2004/033685A1, WO 2004/074322A1, and WO 2013/057586A1, the contents of which are incorporated by reference in their entirety.

In addition, the peptides and/or the TCRs or antibodies or other binding molecules of the present description can be used to verify a pathologist's diagnosis of a cancer based on a biopsied sample.

The antibodies or TCRs may also be used for in vivo diagnostic assays. Generally, the antibody or TCR is labeled with a radionucleotide (such as $^{111}$In, $^{99}$Tc, $^{14}$C, $^{131}$I, $^{3}$H, $^{32}$P or $^{35}$S)) so that the tumor can be localized using immunoscintiography. In one embodiment, antibodies or fragments thereof bind to the extracellular domains of two or more targets of a protein selected from the group consisting of the above-mentioned proteins, and the affinity value (Kd) is less than 1×10 µM.

Antibodies or TCRs for diagnostic use may be labeled with probes suitable for detection by various imaging methods. Methods for detection of probes include, but are not limited to, fluorescence, light, confocal and electron microscopy; magnetic resonance imaging and spectroscopy; fluoroscopy, computed tomography and positron emission tomography. Suitable probes include, but are not limited to, fluorescein, rhodamine, eosin and other fluorophores, radioisotopes, gold, gadolinium and other lanthanides, paramagnetic iron, fluorine-18 and other positron-emitting radionuclides. Additionally, probes may be bi- or multi-functional and be detectable by more than one of the methods listed. These antibodies and/or TCRs may be directly or indirectly labeled with said probes. Attachment of probes to the antibodies and/or TCRs includes covalent attachment of the probe, incorporation of the probe into the antibody or TCR, and the covalent attachment of a chelating compound for binding of probe, amongst others well recognized in the art. For immunohistochemistry, the disease tissue sample may be fresh or frozen or may be embedded in paraffin and fixed with a preservative such as formalin. The fixed or embedded section contains the sample are contacted with a labeled primary antibody and secondary antibody, wherein the antibody is used to detect the expression of the proteins in situ.

EXAMPLES

Allo-reactive settings can be used to circumvent self-tolerance and yield T-cells with a higher avidity when compared to T-cells derived from autologous settings, i.e., patients. Examples of such settings include in vitro generation of allo-HLA reactive, peptide-specific T-cells (Sadovnikova et al. 1998; Savage et al. 2004; Wilde et al. 2012), and immunization of mice transgenic for human-MHC or human TCR (Stanislawski et al. 2001; Li et al. 2010).

Example 1

In vitro generation of allo-HLA reactive, peptide-specific T-cells (Savage et al. 2004) PBMCs from HLA-A*02-positive and HLA-A*02-negative healthy donors were used after obtaining informed consent. Recombinant biotinylated HLA-A2 class I monomers and A2 fluorescent tetramers containing IGF2BP3-001 were obtained from MBLI (Woburn, Mass.). PBMCs were incubated with anti-CD20SA diluted in phosphate buffered saline (PBS) for 1 hour at room temperature, washed, and incubated with the biotinylated A2/IGF2BP3-001 monomers for 30 minutes at room temperature, washed, and plated at 3×10$^6$ cells/well in 24-well plates in RPMI with 10% human AB serum. Interleukin 7 (IL-7; R&D Systems, Minneapolis, Minn.) was added on day 1 at 10 ng/mL and IL-2 (Chiron, Harefield, United Kingdom) was added at 10 U/mL on day 4. Over a 5-week period cells were restimulated weekly with fresh PBMCs, mixed with responder cells at a 1:1 ratio, and plated at 3×10$^6$/well in 24-well plates.

To obtain high avidity T-cells, approximately 10$^6$ PBMCs with HLA-A2/IGF2BP3-001 tetramer-phycoerythrin (PE) (obtained from MBLI) were incubated for 30 minutes at 37° C., followed by anti-CD8-fluorescein isothiocyanate (FITC)/allophycocyanin (APC) for 20 minutes at 4° C., followed by fluorescence activated cell sorting (FACS)-Calibur analysis. Sorting was done with a FACS-Vantage (Becton Dickinson, Cowley, Oxford, United Kingdom). Sorted tetramer-positive cells were expanded in 24-well plates using, per well, 2×10$^5$ sorted cells, 2×10$^6$ irradiated A2-negative PBMCs as feeders, 2×10$^4$ CD3/CD28 beads/ mL (Dynal, Oslo Norway), and IL-2 (1000 U/mL). The high avidity T-cells, thus obtained, were then used to identify and isolate TCRs using techniques known in the art, such as single cell 5' RACE (Rapid Amplification of cDNA Ends). Non-redundant TCR DNAs were then analyzed for amino acid/DNA sequences determination and cloning into expression vectors using methods well known in the art.

Example 2: Cloning of TCRs

Methods of cloning TCRs are known in the art, for example, as described in U.S. Pat. No. 8,519,100, which is hereby incorporated by reference in its entirety for said methods. The alpha chain variable region sequence specific oligonucleotide A1 (ggaattccatatgagtcaacaaggagaagaagatcc SEQ ID NO:22) which encodes the restriction site NdeI, an introduced methionine for efficient initiation of expression in bacteria, and an alpha chain constant region sequence specific oligonucleotide A2 (ttgtcagtcgacttagagtctctcagctgg-tacacg SEQ ID NO:23) which encodes the restriction site SalI are used to amplify the alpha chain variable region. In the case of the beta chain, a beta chain variable region sequence specific oligonucleotide B1 (tctctcatatggatggtg-gaattactcaatccccaa SEQ ID NO:24) which encodes the restriction site NdeI, an introduced methionine for efficient initiation of expression in bacteria, and a beta chain constant region sequence specific oligonucleotide B2 (tagaaaccggtg-gccaggcacaccagtgtggc SEQ ID NO:25) which encodes the restriction site AgeI are used to amplify the beta chain variable region.

The DNA sequences encoding the TCR alpha chain cut with NdeI and SalI are ligated into pGMT7+Cα vector, which was cut with NdeI and XhoI. The DNA sequences encoding the TCR beta chain cut with NdeI and AgeI was ligated into separate pGMT7+Cβ vector, which was also cut with NdeI and AgeI. Ligated plasmids are transformed into competent *Escherichia coli* strain XL1-blue cells and plated out on LB/agar plates containing 100 μg/ml ampicillin. Following incubation overnight at 37° C., single colonies are picked and grown in 10 ml LB containing 100 μg/ml ampicillin overnight at 37° C. with shaking. Cloned plasmids are purified using a Miniprep kit (Qiagen) and the insert is sequenced using an automated DNA sequencer (Lark Technologies).

TCR R10P1A7, encoding tumor specific TCR-alpha and TCR-beta chains, were isolated and amplified from T-cells of healthy donors. Cells from healthy donors were in vitro stimulated according to the method described in Walter et. al. 2003. Target-specific cells were single-cell sorted using target-specific multimers for subsequent TCR isolation. TCR sequences were isolated via 5' RACE by standard methods as described by e.g. Molecular Cloning a laboratory manual fourth edition by Green and Sambrook. TCR R10P1A7 was isolated from a HLA-A2 negative donor. The alpha and beta variable regions of TCRs R20P1H7, R7P1D5 and R10P2G12 were sequenced.

The R10P1A7 TCR alpha variable domain was found to have an amino acid sequence corresponding to residues 22-130 of SEQ ID NO:2. The R10P1A7 TCR beta variable domain was found to have an amino acid sequence corresponding to residues 26-139 of SEQ ID NO:10.

Phage display can be used to generate libraries of TCR variants to identify high affinity mutants. The TCR phage display and screening methods described in (Li et al, (2005) Nature Biotech 23 (3): 349-354) can be applied to a reference TCR selected from the TCRs described in Table 1.

For example, all three CDR regions of the alpha chain sequence of SEQ ID NO:2 and all three CDR regions of the beta chain sequence of SEQ ID NO:10 can be targeted by mutagenesis, and each CDR library panned and screened separately.

Accordingly, TCRs with affinities and/or binding half-lives at least twice that of the reference TCR (and therefore impliedly at least twice that of the native TCR) can be identified.

TCR heterodimers are refolded using the method including the introduced cysteines in the constant regions to provide the artificial inter-chain disulphide bond. In that way TCRs are prepared, consisting of (a) the reference TCR beta chain, together with mutated alpha chains; (b) the reference TCR alpha chain together with mutated beta chains; and (c) various combinations of beta and alpha chains including the mutant variable domains.

The interaction between high affinity soluble disulfide-linked TCRs, and TCR variants, and the native peptide KIQEILTQV (SEQ ID NO: 1) HLA complex can be analyzed using the BIAcore method.

High avidity TCR variants can also be selected from a library of CDR mutants by yeast, or T-cell display (Holler et al. 2003; Chervin et al. 2008). Candidate TCR variants, thus, provide guidance to design mutations of the TCR's CDRs to obtain high avidity TCR variants (Robbins et al. 2008; Zoete et al. 2007).

Example 3: Autologous T-Cell Engineering

T-cells can be engineered to express high avidity TCRs (so-called TCR therapies) or protein-fusion derived chimeric antigen receptors (CARs) that have enhanced antigen specificity to MHC I/IGF2BP3-001 complex or MHC II/IGF2BP3-001 complex. In an aspect, this approach overcomes some of the limitations associated with central and peripheral tolerance, and generates T-cells that will be more efficient at targeting tumors without the requirement for de novo T-cell activation in the patient.

In one aspect, to obtain T-cells expressing TCRs of the present description, nucleic acids encoding the tumor specific TCR-alpha and/or TCR-beta chains identified and isolated, as described in Examples 1-2, are cloned into expression vectors, such as gamma retrovirus or lentivirus. The recombinant viruses are generated and then tested for functionality, such as antigen specificity and functional avidity. An aliquot of the final product is then used to transduce the target T-cell population (generally purified from patient PBMCs), which is expanded before infusion into the patient.

In another aspect, to obtain T-cells expressing TCRs of the present description, TCR RNAs were synthesized by techniques known in the art, e.g., in vitro transcription systems. The in vitro-synthesized TCR RNAs were then introduced into primary CD8+ T-cells obtained from healthy donors by electroporation to re-express tumor specific TCR-alpha and/or TCR-beta chains.

Figure 5:
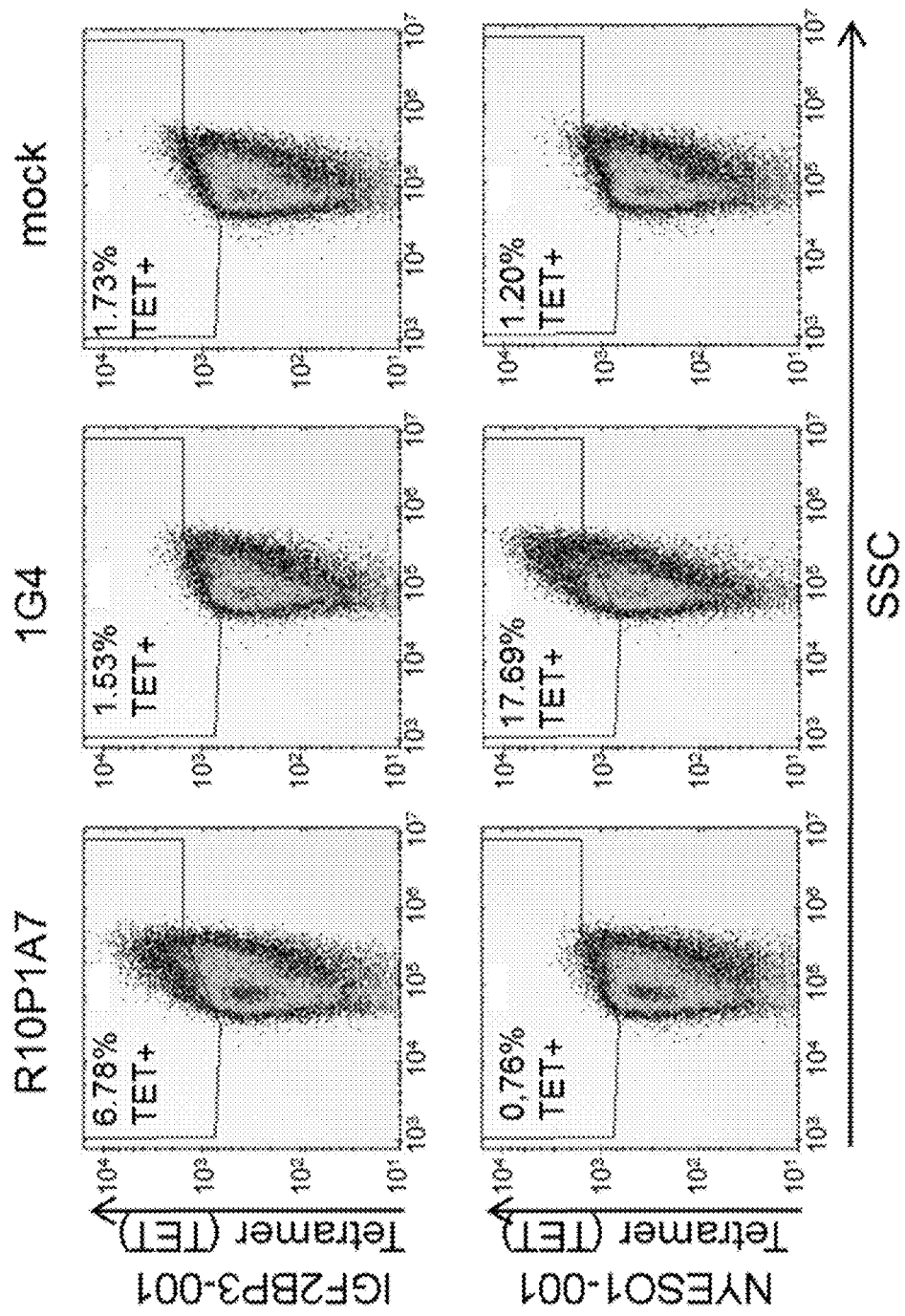
FIG. 5 shows MHC/IGF2BP3-001 tetramer or MHC/NYESO1-001 tetramer staining of CD8+ T-cells electroporated with alpha and beta chain RNA of TCR R10P1A7 (Table 1). CD8+ T-cells transformed with RNA of 1G4 TCR that specifically binds to MHC/NYESO1-001 complex and mock transformations served as controls.

To test whether exogenous TCRs were functionally expressed on cell surface of the transformed T-cells, a tetramer staining technique was used to detect MHC/IGF2BP3-001-binding T-cells. As shown in FIG. 5 and Table 2, a higher percentage of CD3-positive specific T-cell population, i.e., 6.78% was observed in TCR-expressing CD8+ T-cells by fluorescent-labeled MHC/IGF2BP3-001 tetramer staining than that with MHC/unrelated peptide (e.g., NYESO1-001) tetramers, e.g., 1.53%, or mock control, e.g., 1.73%. As a control, primary CD8+ T-cells transformed with a control TCR, 1G4 TCR, which is known to bind specifically to MHC/NYESO1-001 complex, was readily detected by MHC/NYESO1-001 tetramer, i.e., 17.69%. These results indicate that TCR R10P1A7 is expressed on T-cell surface and can bind specifically to MHC/IGF2BP3-001 complex. The alpha and beta chains of TCR 1G4 are shown in SEQ ID NO:20 and SEQ ID NO:21, respectively:

```
1G4 alpha chain (SEQ ID NO: 20):
METLLGLLILWLQLQWVSSKQEVTQIPAALSVPEGENLVLNCSFTDSAIY

NLQWFRQDPGKGLTSLLLIQSSQREQTSGRLNASLDKSSGRSTLYIAASQ

PGDSATYLCAVRPTSGGSYIPTFGRGTSLIVHPYIQNPDPAVYQLRDSKS

SDKSVCLFTDFDSQTNVSQSKDSDVYITDKTVLDMRSMDFKSNSAVAWSN

KSDFACANAFNNSIIPEDTFFPSPESSCDVKLVEKSFETDTNLNFQNLSV

IGFRILLLKVAGFNLLMTLRLWSS

1G4 beta chain (SEQ ID NO: 21):
MSIGLLCCAALSLLWAGPVNAGVTQTPKFQVLKTGQSMTLQCAQDMNHEY

MSWYRQDPGMGLRLIHYSVGAGITDQGEVPNGYNVSRSTTEDFPLRLLSA

APSQTSVYFCASSYVGNTGELFFGEGSRLTVLEDLKNVFPPEVAVFEPSE

AEISHTQKATLVCLATGFYPDHVELSWWVNGKEVHSGVSTDPQPLKEQPA

LNDSRYCLSSRLRVSATFWQNPRNHFRCQVQFYGLSENDEWTQDRAKPVT

QIVSAEAWGRADCGFTSESYQQGVLSATILYEILLGKATLYAVLVSALVL

MAMVKRKDSRG
```

To determine specificity and affinity of TCRs, the transformed CD8+ T-cells were co-incubated with IGF2BP3-001-loaded target cells or with target cells loaded with homologous but unrelated peptide CLUA-001 (SEQ ID NO:26), CHCHD6-001 (SEQ ID NO:27), CDC42BPG-001 (SEQ ID NO:28), PARP14-002 (SEQ ID NO:29), SYNE2-001 (SEQ ID NO:30), IFT7-001 (SEQ ID NO:31), DHRS12-001 (SEQ ID NO:32), STX12-001 (SEQ ID NO:33), EEA-001 (SEQ ID NO:34), SENP7-001 (SEQ ID NO:35), or control peptide NYESO1-001 (SEQ ID NO:36), followed by IFN-γ release assay. Unloaded target cells and CD8+ T-cells alone served as controls. IFN-γ secretion from CD8+ T-cells is indicative of T-cell activation with cytotoxic activity.

TABLE 2

| TCR Code | Donor/HLA-A2 (+ or −) | IFNγ (pg/ml) | EC50 | % IGF2BP3-001 TET-positive primary CD8+ T-cells | % NYESO1-001 TET-positive primary CD8+ T-cells |
|---|---|---|---|---|---|
| R10P1A7 | HBC-688/(−) | 175 | ~1 nM | 6.78 | 1.53 |

Figure 6:
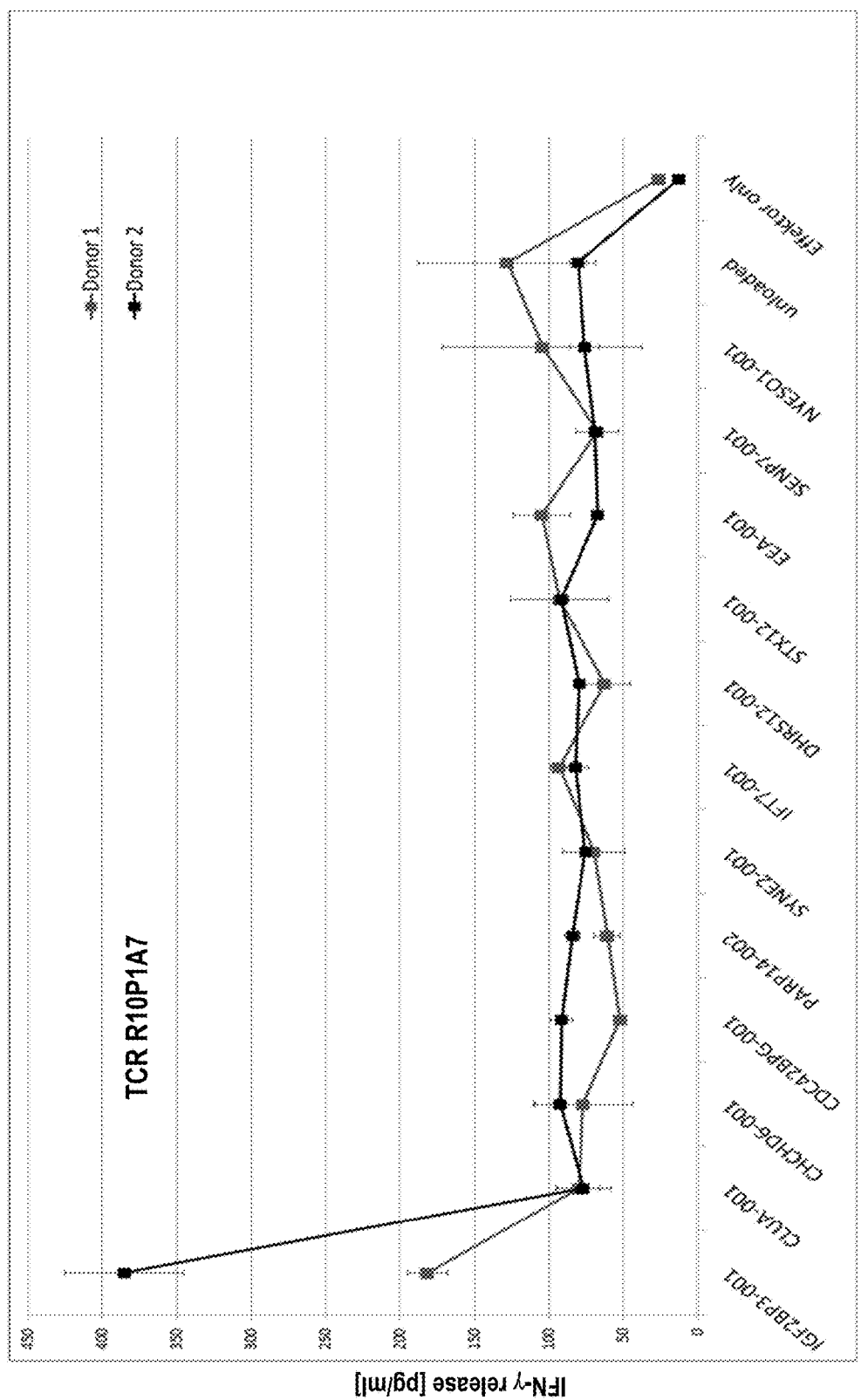
FIG. 6 shows IFNγ release from CD8+ T-cells electroporated with alpha and beta chain RNA of TCR R10P1A7 (Table 1) after co-incubation with target cells loaded with IGF2BP3-001 peptide (SEQ ID NO:1) or homologous but unrelated peptide CLUA-001 (SEQ ID NO:26), CHCHD6-001 (SEQ ID NO:27), CDC42BPG-001 (SEQ ID NO:28), PARP14-002 (SEQ ID NO:29), SYNE2-001 (SEQ ID NO:30), IFT7-001 (SEQ ID NO:31), DHRS12-001 (SEQ ID NO:32), STX12-001 (SEQ ID NO:33), EEA-001 (SEQ ID NO:34), SENP7-001 (SEQ ID NO:35), or control peptide NYESO1-001 (SEQ ID NO:36). IFNγ release data were obtained with CD8+ T-cells derived from two different donors. RNA electroporated CD8+ T-cells alone or in co-incubation with unloaded target cells served as controls.

As shown in FIG. 6 primary CD8+ T-cells electroporated with RNA encoding TCR R10P1A7 of the present disclosure, after co-incubation with IGF2BP3-001-loaded target cells, released much higher levels of IFN-γ than that stimulated by control peptide-loaded target cells, and the controls. Target peptide titration analysis showed EC50 at about 1 nM (Table 2). These results suggest that TCR R10P1A7 of the present invention can activate cytotoxic T-cell activity, e.g., IFN-γ release, through specific interaction with the MHC/IGF2BP3-001 complex.

To determine the binding motif of TCR R10P1A7 for the MHC/IGF2BP3-001 complex, positional alanine scanning analysis was performed at each of the 9 amino acids of the IGF2BP3-001 peptide. Alanine-substituted IGF2BP3-001 peptides are shown in Table 3.

TABLE 3

| Position: | 1 | 2 | 3 | 4 | 5 | 6 | 7 | 8 | 9 |
|---|---|---|---|---|---|---|---|---|---|
| IGF2BP3-001 (SEQ ID NO: 1) | K | I | Q | E | I | L | T | Q | V |
| IGF2BP3-001 A1 (SEQ ID NO: 37) | A | I | Q | E | I | L | T | Q | V |
| IGF2BP3-001 A2 (SEQ ID NO: 38) | K | A | Q | E | I | L | T | Q | V |
| IGF2BP3-001 A3 (SEQ ID NO: 39) | K | I | A | E | I | L | T | Q | V |
| IGF2BP3-001 A4 (SEQ ID NO: 40) | K | I | Q | A | I | L | T | Q | V |
| IGF2BP3-001 A5 (SEQ ID NO: 41) | K | I | Q | E | A | L | T | Q | V |
| IGF2BP3-001 A6 (SEQ ID NO: 42) | K | I | Q | E | I | A | T | Q | V |
| IGF2BP3-001 A7 (SEQ ID NO: 43) | K | I | Q | E | I | L | A | Q | V |
| IGF2BP3-001 A8 (SEQ ID NO: 44) | K | I | Q | E | I | L | T | A | V |
| IGF2BP3-001 A9 (SEQ ID NO: 45) | K | I | Q | E | I | L | T | Q | A |

Briefly, CD8+ T-cells transformed with TCR R10P1A7 were co-incubated with target cells loaded with IGF2BP3-001, IGF2BP3-001-A1 to IGF2BP3-001-A9, or a control peptide NYESO1-001 peptide, followed by IFNγ release assay, as described above.

Figure 7:
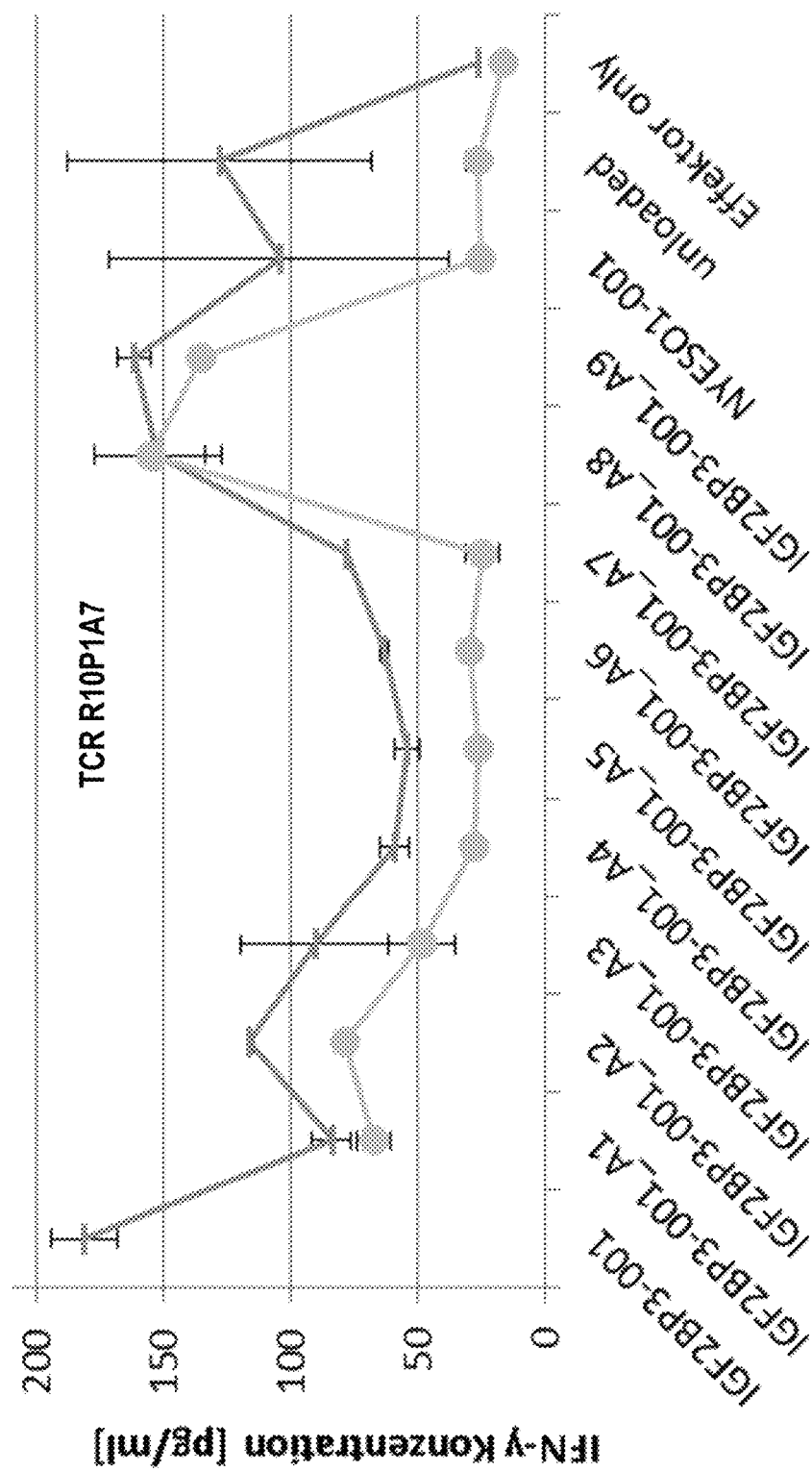
FIG. 7 shows IFNγ release from CD8+ T-cells electroporated with alpha and beta chain RNA of TCR R10P1A7 after co-incubation with target cells loaded with IGF2BP3-001 (SEQ ID NO:1) or various IGF2BP3-001 alanine-substitution variants at positions 1-9 of SEQ ID NO:1. RNA-electroporated CD8+ T-cells alone or in co-incubation with target cells loaded with control peptide NYESO1-001 or unloaded target cells served as controls. IFNγ release data were obtained with CD8+ T-cells derived from two different donors.

Results of positional alanine scanning analysis on TCR R10P1A7 is shown in FIG. 7, and summarized in Table 4.

TABLE 4

| TCR | IGF2BP3-001 positions enable TCR binding |
|---|---|
| R10P1A7 | 1, 3-7 |

A genome-wide screen for A*02-binding peptides for TCR R10P1A7 with an identical motif revealed no potentially cross-reactive peptides. These results suggest that the TCR described herein exhibits a very specific recognition pattern with a reduced risk of off-target effects.

To determine efficacy of T-cells expressing TCRs described herein, primary CD8+ T-cells electroporated with RNA of TCR R10P1A7 were co-incubated with different human cancer cell lines, e.g., A-375 (human melanoma cell line) and T98G (human glioblastoma cell line), which are HLA-A2-positive and IGF2BP3-001 (target)-positive, and SK-BR-3 (human breast cancer cell line), which is HLA-A2-negative and IGF2BP3-001-negative, followed by IFNγ release assay.

Figure 8:
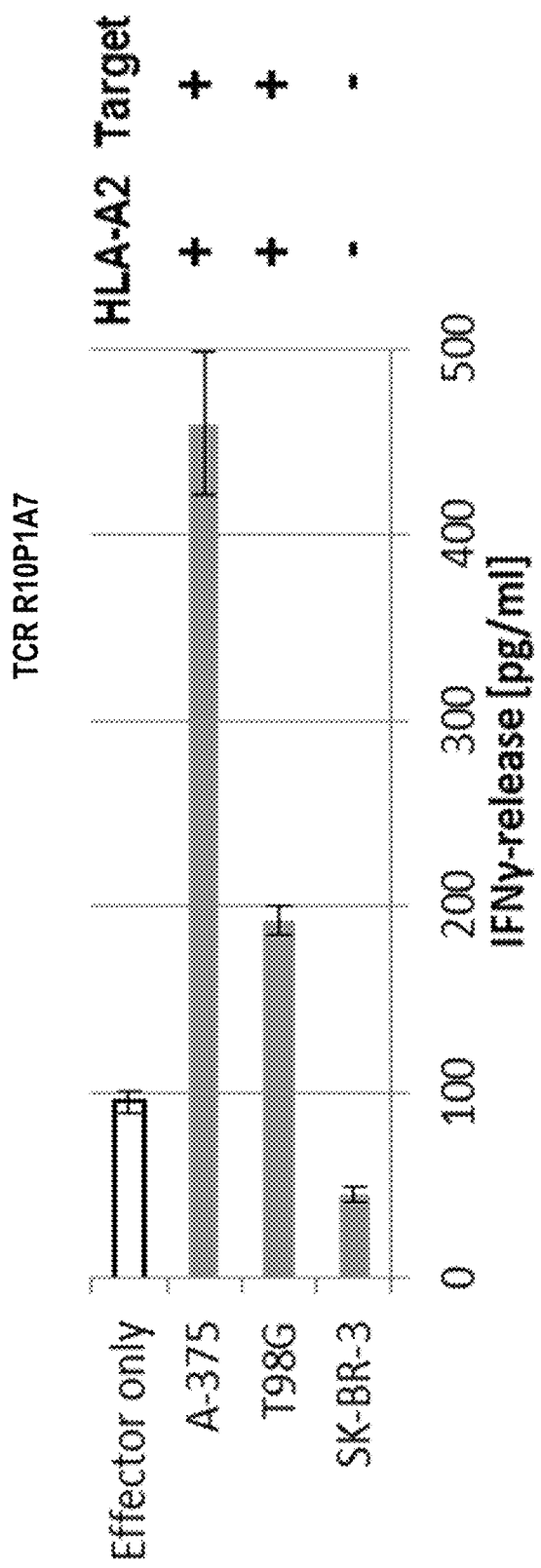
FIG. 8 shows IFNγ release from CD8+ T-cells electroporated with alpha and beta chain RNA of TCR R10P1A7 (Table 1) after co-incubation with A-375 melanoma cell line, T98G glioblastoma cell line and SK-BR-3 breast cancer cell line, respectively. RNA-electroporated CD8+ T-cells alone served as a control.

As shown in FIG. 8, IFNγ release was observed in both A-375 and T98G cells, which are HLA-A2-positive and IGF2BP3-001-positive, but not in SK-BR-3 cells, which have basal levels of IFNγ release that is comparable to that of effector cell only control. These results indicate that T-cells expressing TCR R10P1A7 can specifically induce cytotoxic activity targeting cancer cells in a HLA-A2/IGF2BP3-001 specific manner.

The present description provides TCRs that are useful in treating cancers/tumors, preferably melanoma and glioblastoma that over- or exclusively present IGF2BP3-001.

Example 5: Allogeneic T-Cell Engineering

Gamma delta (γδ) T cells, which are non-conventional T lymphocyte effectors implicated in the first line of defense against pathogens, can interact with and eradicate tumor cells in a MHC-independent manner through activating receptors, among others, TCR-gamma and TCR-delta chains. These γδ T cells display a preactivated phenotype that allows rapid cytokine production (IFN-γ, TNF-α) and strong cytotoxic response upon activation. These T-cells have anti-tumor activity against many cancers and suggest that γδ T cell-mediated immunotherapy is feasible and can induce objective tumor responses. (Braza et al. 2013). ture on aAPC, and these subsets displayed differences in memory phenotype and reactivity to tumors in vitro and in vivo. (Deniger et al. 2014).

In addition, γδ T-cells are amenable to genetic modification as evidenced by introduction of TCR-alpha and TCR-beta chains. (Hiasa et al. 2009). Another aspect of the present description relates to production of γδ T-cells expressing TCR-alpha and TCR-beta that bind to IGF2BP3-001. To do so, γδ T-cells are expanded by methods described by Deniger et al. 2014, followed by transducing the recombinant viruses expressing the TCRs that bind to IGF2BP3-001 (as described in Example 3) into the expanded γδ T-cells. The virus-transduced γδ T-cells are then infused into the patient.

Example 6: Lentiviral Constructs and Analysis of Expression

Briefly, two test constructs were made ("R10"). These constructs were then used to produce lentiviral sups with good titer and productivity. The lentiviral sups were then used to transduce primary T-cells (2 donors) with subsequent surface expression of the TCR based on tetramer binding by flow cytometry.

TABLE 5A

Lentiviral constructs and control-respective donors as tested (lines of tables correspond to constructs)

| | | Name | Lot # | p24 (ng/ml) PN | qPCR HEK (TU/ml) | qPCR SUPT 1 (TU/ml) | Volume to Achieve MOI 50 (ul) |
|---|---|---|---|---|---|---|---|
| 1863R | IGF2BP3 | MSCV-R10P1A7A-2A-R10P1A7B-WPRE | 0139-0516-230 | 35590 | 7.2E+09 | 1.3E+10 | 3.9 |
| 1864R | | MSCV-R10P1A7B-2A-R10P1A7A-WPRE | 0139-0516-231 | 55724 | 9.7E+09 | 1.6E+10 | 3.2 |
| VSVG-GFP | Control | EF1a-GFP | 0139-0616-250 | 62176 | 1.3E+09 | 8.21E+08 | 60.9 |

Donor 1

| Total number of cells at time of flow | Viability | % of CD3+ | % of CD3+ Tet+ | % of CD4+ | % of CD8+ | % of CD8+ Tet+ |
|---|---|---|---|---|---|---|
| 126234 | 99.36% | 98.05 | 2.3 | 40.75 | 57.3 | 3.93 |
| 98272 | 99.08% | 97.78 | 15.15 | 39.88 | 57.9 | 21.99 |
| 92038 | 95.70% | 98.81 | 0.21 | | | 0.04 |

Donor 2

| Total number of cells at time of flow | Viability | % of CD3+ | % of CD3+ Tet+ | % of CD4+ | % of CD8+ | % of CD8+ Tet+ |
|---|---|---|---|---|---|---|
| 132888 | 98.47 | 97.98 | 0.99 | 26.8 | 69.35 | 1.79 |
| 135418 | 98.74 | 98.01 | 8.12 | 29.47 | 71.2 | 11.72 |
| 104276 | 99.13 | 98.17 | 0 | 27.82 | 3.59 | 0.06 |

Recent advances using immobilized antigens, agonistic monoclonal antibodies (mAbs), tumor-derived artificial antigen presenting cells (aAPC), or combinations of activating mAbs and aAPC have been successful in expanding gamma delta T-cells with oligoclonal or polyclonal TCR repertoires. For example, immobilized major histocompatibility complex Class-I chain-related A was a stimulus for γδ T-cells expressing TCRδ1 isotypes, and plate-bound activating antibodies have expanded Vδ1 and Vδ2 cells ex vivo. Clinically sufficient quantities of TCRδ1, TCRδ2, and TCRδ1$^{neg}$TCRδ2$^{neg}$ have been produced following co-cul-

REFERENCE LIST

Adair S J, Hogan K T (2009). Treatment of ovarian cancer cell lines with 5-aza-2'-deoxycytidine upregulates the expression of cancer-testis antigens and class I major histocompatibility complex-encoded molecules. Cancer Immunol. Immunother. 58, 589-601.

Alves P M, Levy N, Bouzourene H, Viatte S, Bricard G, Ayyoub M, Vuilleumier H, Givel J C, Halkic N, Speiser D E, Romero P, Levy F (2007). Molecular and immunological evaluation of the expression of cancer/testis gene products in human colorectal cancer. Cancer Immunol. Immunother. 56, 839-847.

Andrade V C, Vettore A L, Felix R S, Almeida M S, Carvalho F, Oliveira J S, Chauffaille M L, Andriolo A, Caballero O L, Zago M A, Colleoni G W (2008). Prognostic impact of cancer/testis antigen expression in advanced stage multiple myeloma patients. Cancer Immun. 8, 2.

Barrow C, Browning J, MacGregor D, Davis I D, Sturrock S, Jungbluth A A, Cebon J (2006). Tumor antigen expression in melanoma varies according to antigen and stage. Clin Cancer Res 12, 764-771.

Bellati F, Napoletano C, Tarquini E, Palaia I, Landi R, Manci N, Spagnoli G, Rughetti A, Panici P B, Nuti M (2007). Cancer testis antigen expression in primary and recurrent vulvar cancer: association with prognostic factors. Eur. J Cancer 43, 2621-2627.

Bergeron A, Picard V, LaRue H, Harel F, Hovington H, Lacombe L, Fradet Y (2009).

Bode P K, Thielken A, Brandt S, Barghorn A, Lohe B, Knuth A, Moch H (2014). Cancer testis antigen expression in testicular germ cell tumorigenesis. Mod. Pathol. 27, 899-905.

Chitale D A, Jungbluth A A, Marshall D S, Leitao M M, Hedvat C V, Kolb D, Spagnoli G C, Iversen K, Soslow R A (2005). Expression of cancer-testis antigens in endometrial carcinomas using a tissue microarray. Mod. Pathol. 18, 119-126.

Coral S, Parisi G, Nicolay H J, Colizzi F, Danielli R, Fratta E, Covre A, Taverna P, Sigalotti L, Maio M (2013). Immunomodulatory activity of SGI-110, a 5-aza-2'-deoxycytidine-containing demethylating dinucleotide. Cancer Immunol. Immunother. 62, 605-614.

Cuffel C, Rivals J P, Zaugg Y, Salvi S, Seelentag W, Speiser D E, Lienard D, Monnier P, Romero P, Bron L, Rimoldi D (2011). Pattern and clinical significance of cancer-testis gene expression in head and neck squamous cell carcinoma. Int. J Cancer 128, 2625-2634.

Forghanifard M M, Gholamin M, Farshchian M, Moaven O, Memar B, Forghani M N, Dadkhah E, Naseh H, Moghbeli M, Raeisossadati R, Abbaszadegan M R (2011). Cancer-testis gene expression profiling in esophageal squamous cell carcinoma: identification of specific tumor marker and potential targets for immunotherapy. Cancer Biol Ther. 12, 191-197.

Gerdemann U, Katari U, Christin A S, Cruz C R, Tripic T, Rousseau A, Gottschalk S M, Savoldo B, Vera J F, Heslop H E, Brenner M K, Bollard C M, Rooney C M, Leen A M (2011). Cytotoxic T lymphocytes simultaneously targeting multiple tumor-associated antigens to treat EBV negative lymphoma. Mol. Ther. 19, 2258-2268.

Gunda V, Cogdill A P, Bernasconi M J, Wargo J A, Parangi S (2013). Potential role of 5-aza-2'-deoxycytidine induced MAGE-A4 expression in immunotherapy for anaplastic thyroid cancer. Surgery 154, 1456-1462.

Gure A O, Chua R, Williamson B, Gonen M, Ferrera C A, Gnjatic S, Ritter G, Simpson A J, Chen Y T, Old L J, Altorki N K (2005). Cancer-testis genes are coordinately expressed and are markers of poor outcome in non-small cell lung cancer. Clin Cancer Res 11, 8055-8062.

Hoffmann N E, Sheinin Y, Lohse C M, Parker A S, Leibovich B C, Jiang Z, Kwon E D (2008). External validation of IMP3 expression as an independent prognostic marker for metastatic progression and death for patients with clear cell renal cell carcinoma. Cancer 112, 1471-1479.

Jacobs J F, Grauer O M, Brasseur F, Hoogerbrugge P M, Wesseling P, Gidding C E, van de Rakt M W, Figdor C G, Coulie P G, de Vries I J, Adema G J (2008). Selective cancer-germ line gene expression in pediatric brain tumors. J Neurooncol. 88, 273-280.

Kang J, Lee H J, Kim J, Lee J J, Maeng L S (2015). Dysregulation of X chromosome inactivation in high grade ovarian serous adenocarcinoma. PLoS. ONE. 10, e0118927.

Kim K, Cho Y M, Park B H, Lee J L, Ro J Y, Go H, Shim J W (2015). Histological and immunohistochemical markers for progression prediction in transurethrally resected high-grade non-muscle invasive bladder cancer. Int. J Clin Exp. Pathol. 8, 743-750.

Kubuschok B, Xie X, Jesnowski R, Preuss K D, Romeike B F, Neumann F, Regitz E, Pistorius G, Schilling M, Scheunemann P, Izbicki J R, Lohr J M, Pfreundschuh M (2004). Expression of cancer testis antigens in pancreatic carcinoma cell lines, pancreatic adenocarcinoma and chronic pancreatitis. Int. J Cancer 109, 568-575.

Li M, Yuan Y H, Han Y, Liu Y X, Yan L, Wang Y, Gu J (2005). Expression profile of cancer-testis genes in 121 human colorectal cancer tissue and adjacent normal tissue. Clin Cancer Res 11, 1809-1814.

Lifantseva N, Koltsova A, Krylova T, Yakovleva T, Poljanskaya G, Gordeeva O (2011). Expression patterns of cancer-testis antigens in human embryonic stem cells and their cell derivatives indicate lineage tracks. Stem Cells Int. 2011, 795239.

Luftl M, Schuler G, Jungbluth A A (2004). Melanoma or not? Cancer testis antigens may help. Br. J Dermatol. 151, 1213-1218.

Mischo A, Kubuschok B, Ertan K, Preuss K D, Romeike B, Regitz E, Schormann C, de B D, Wadle A, Neumann F, Schmidt W, Renner C, Pfreundschuh M (2006). Prospective study on the expression of cancer testis genes and antibody responses in 100 consecutive patients with primary breast cancer. Int. J Cancer 118, 696-703.

Mitchell R T, Camacho-Moll E, MacDonald J, Anderson R A, Kelnar C J, O'Donnell M, Sharpe R M, Smith L B, Grigor K M, Wallace W H, Stoop H, Wolffenbuttel K P, Donat R, Saunders P T, Looijenga L H (2014). Intratubular germ cell neoplasia of the human testis: heterogeneous protein expression and relation to invasive potential. Mod. Pathol. 27, 1255-1266.

Mizukami Y, Kono K, Daigo Y, Takano A, Tsunoda T, Kawaguchi Y, Nakamura Y, Fujii H (2008). Detection of novel cancer-testis antigen-specific T-cell responses in TIL, regional lymph nodes, and PBL in patients with esophageal squamous cell carcinoma. Cancer Sci.

Nishikawa H, Maeda Y, Ishida T, Gnjatic S, Sato E, Mori F, Sugiyama D, Ito A, Fukumori Y, Utsunomiya A, Inagaki H, Old L J, Ueda R, Sakaguchi S (2012). Cancer/testis antigens are novel targets of immunotherapy for adult T-cell leukemia/lymphoma. Blood 119, 3097-3104.

Oba-Shinjo S M, Caballero O L, Jungbluth A A, Rosemberg S, Old L J, Simpson A J, Marie S K (2008). Cancer-testis (C T) antigen expression in medulloblastoma. Cancer Immun. 8, 7.

Peikert T, Specks U, Farver C, Erzurum S C, Comhair S A (2006). Melanoma antigen A4 is expressed in non-small cell lung cancers and promotes apoptosis. Cancer Res 66, 4693-4700.

Peng J R, Chen H S, Mou D C, Cao J, Cong X, Qin L L, Wei L, Leng X S, Wang Y, Chen W F (2005). Expression of cancer/testis (C T) antigens in Chinese hepatocellular carcinoma and its correlation with clinical parameters. Cancer Lett. 219, 223-232.

Perez D, Herrmann T, Jungbluth A A, Samartzis P, Spagnoli G, Demartines N, Clavien P A, Marino S, Seifert B, Jaeger D (2008). Cancer testis antigen expression in gastrointestinal stromal tumors: new markers for early recurrence. Int. J Cancer 123, 1551-1555.

Prasad M L, Jungbluth A A, Patel S G, Iversen K, Hoshaw-Woodard S, Busam K J (2004). Expression and significance of cancer testis antigens in primary mucosal melanoma of the head and neck. Head Neck 26, 1053-1057.

Pryor J G, Bourne P A, Yang Q, Spaulding B O, Scott G A, Xu H (2008). IMP-3 is a novel progression marker in malignant melanoma. Mod. Pathol. 21, 431-437.

Rammensee H G, Bachmann J, Emmerich N P, Bachor O A, Stevanovic S (1999). SYFPEITHI: database for MHC ligands and peptide motifs. Immunogenetics 50, 213-219.

Rammensee H G, Bachmann J, Stevanovic S (1997). MHC Ligands and Peptide Motifs. (Heidelberg, Germany: Springer-Verlag).

Resnick M B, Sabo E, Kondratev S, Kerner H, Spagnoli G C, Yakirevich E (2002). Cancer-testis antigen expression in uterine malignancies with an emphasis on carcinosarcomas and papillary serous carcinomas. Int. J Cancer 101, 190-195.

Sarcevic B, Spagnoli G C, Terracciano L, Schultz-Thater E, Heberer M, Gamulin M, Krajina Z, Oresic T, Separovic R, Juretic A (2003). Expression of cancer/testis tumor associated antigens in cervical squamous cell carcinoma. Oncology 64, 443-449.

Schirmer U, Fiegl H, Pfeifer M, Zeimet A G, Muller-Holzner E, Bode P K, Tischler V, Altevogt P (2013). Epigenetic regulation of L1CAM in endometrial carcinoma: comparison to cancer-testis (CT-X) antigens. BMC. Cancer 13, 156.

Shafer J A, Cruz C R, Leen A M, Ku S, Lu A, Rousseau A, Heslop H E, Rooney C M, Bollard C M, Foster A E (2010). Antigen-specific cytotoxic T lymphocytes can target chemoresistant side-population tumor cells in Hodgkin lymphoma. Leuk. Lymphoma 51, 870-880.

Sharma P, Shen Y, Wen S, Bajorin D F, Reuter V E, Old L J, Jungbluth A A (2006). Cancer-testis antigens: expression and correlation with survival in human urothelial carcinoma. Clin Cancer Res 12, 5442-5447.

Shigematsu Y, Hanagiri T, Shiota H, Kuroda K, Baba T, Mizukami M, So T, Ichiki Y, Yasuda M, So T, Takenoyama M, Yasumoto K (2010). Clinical significance of cancer/testis antigens expression in patients with non-small cell lung cancer. Lung Cancer 68, 105-110.

Shirakura Y, Mizuno Y, Wang L, Imai N, Amaike C, Sato E, Ito M, Nukaya I, Mineno J, Takesako K, Ikeda H, Shiku H (2012). T-cell receptor gene therapy targeting melanoma-associated antigen-A4 inhibits human tumor growth in non-obese diabetic/SCID/gammacnull mice. Cancer Sci. 103, 17-25.

Soga N, Hori Y, Yamakado K, Ikeda H, Imai N, Kageyama S, Nakase K, Yuta A, Hayashi N, Shiku H, Sugimura Y (2013). Limited expression of cancer-testis antigens in renal cell carcinoma patients. Mol. Clin Oncol 1, 326-330.

Su C, Xu Y, Li X, Ren S, Zhao C, Hou L, Ye Z, Zhou C (2015). Predictive and prognostic effect of CD133 and cancer-testis antigens in stage Ib-IIIA non-small cell lung cancer. Int. J Clin Exp. Pathol. 8, 5509-5518.

Walter S, Herrgen L, Schoor O, Jung G, Wernet D, Bühring H J, Rammensee H G, Stevanović S. (2003). Cutting edge: predetermined avidity of human CD8 T cells expanded on calibrated MHC/anti-CD28-coated microspheres. J Immunol. 171(10), 4974-8

Wang M, Li J, Wang L, Chen X, Zhang Z, Yue D, Ping Y, Shi X, Huang L, Zhang T, Yang L, Zhao Y, Ma X, Li D, Fan Z, Zhao L, Tang Z, Zhai W, Zhang B, Zhang Y (2015). Combined cancer testis antigens enhanced prediction accuracy for prognosis of patients with hepatocellular carcinoma. Int. J Clin Exp. Pathol. 8, 3513-3528.

Yamada R, Takahashi A, Torigoe T, Morita R, Tamura Y, Tsukahara T, Kanaseki T, Kubo T, Watarai K, Kondo T, Hirohashi Y, Sato N (2013). Preferential expression of cancer/testis genes in cancer stem-like cells: proposal of a novel sub-category, cancer/testis/stem gene. Tissue Antigens 81, 428-434.

Yantiss R K, Cosar E, Fischer A H (2008). Use of IMP3 in identification of carcinoma in fine needle aspiration biopsies of pancreas. Acta Cytol. 52, 133-138.

The invention claimed is:

1. A single chain TCR comprising an alpha chain and a beta chain,
   wherein the alpha chain comprises
      SEQ ID NO: 5,
      SEQ ID NO: 6,
      SEQ ID NO: 7, and
   the beta chain comprises
      SEQ ID NO: 13,
      SEQ ID NO: 14, and
      SEQ ID NO: 15.

2. The single chain TCR of claim 1, wherein
   the alpha chain further comprises an alpha constant domain comprising at least 95% sequence identity to SEQ ID NO: 9 and
   the beta chain further comprises a beta constant domain comprising at least 95% sequence identity to SEQ ID NO: 17.

3. The single chain TCR of claim 2, wherein the alpha constant domain comprises an alpha transmembrane domain VIGFRILLLKVAGFNLLMTL (SEQ ID NO:18) and the beta constant domain comprises a beta transmembrane domain TILYEILLGKATLYAVLVSALVL (SEQ ID NO:19).

4. The single chain TCR of claim 1, wherein the alpha chain comprises an alpha variable domain comprising at least 95% sequence identity to SEQ ID NO: 4; and the beta chain comprises a beta variable domain comprising at least 95% sequence identity to SEQ ID NO: 12.

5. The single chain TCR of claim 2, wherein the alpha constant domain consists of SEQ ID NO:9, and the beta constant domain consists of SEQ ID NO:17.

6. The single chain TCR of claim 1, wherein the alpha chain comprises at least 95% sequence identity to SEQ ID NO:2 and the beta chain comprises at least 95% sequence identity to SEQ ID NO:10.

7. The single chain TCR of claim 1, wherein the TCR specifically binds to a IGF2BP3-001 peptide-MHC molecule complex, wherein the IGF2BP3-001 peptide consists of SEQ ID NO:1, and the MHC molecule is an HLA class I molecule.

8. The single chain TCR of claim 1, wherein the alpha chain comprises SEQ ID NO:2; and the beta chain comprises SEQ ID NO:10.

9. The single chain TCR of claim 1, wherein the TCR binds to the peptide sequence consisting of SEQ ID NO: 1 in a complex with an WIC class I molecule.

10. The single chain TCR of claim 1, wherein the alpha chain consists of SEQ ID NO: 2 and the beta chain consists of SEQ ID NO: 10.

11. The single chain TCR of claim 1, wherein
   the CDR1α chain comprises SEQ ID NO: 5,
   the CDR2α chain comprises SEQ ID NO: 6,
   the CDR3α chain comprises SEQ ID NO: 7,
   the CDR1β chain comprises SEQ ID NO: 13,
   the CDR2β chain comprises SEQ ID NO: 14, and
   the CDR3β chain comprises SEQ ID NO: 15.

12. The single chain TCR of claim 11, wherein the TCR specifically binds to the peptide sequence consisting of SEQ ID NO: 1 in a complex with an WIC class I molecule.

13. The single chain TCR of claim 1, wherein
   the CDR1α chain consists of SEQ ID NO: 5,
   the CDR2α chain consists of SEQ ID NO: 6,
   the CDR3α chain consists of SEQ ID NO: 7,
   the CDR1β chain consists of SEQ ID NO: 13,
   the CDR2β chain consists of SEQ ID NO: 14, and
   the CDR3β chain consists of SEQ ID NO: 15.

* * * * *

SEQUENCE LISTING

```
<160> NUMBER OF SEQ ID NOS: 45

<210> SEQ ID NO 1
<211> LENGTH: 9
<212> TYPE: PRT
<213> ORGANISM: Homo sapiens

<400> SEQUENCE: 1

Lys Ile Gln Glu Ile Leu Thr Gln Val
1               5

<210> SEQ ID NO 2
<211> LENGTH: 271
<212> TYPE: PRT
<213> ORGANISM: Homo sapiens

<400> SEQUENCE: 2

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30
```

```
Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
 50                  55                  60

Gln Leu Leu Thr Tyr Ile Phe Ser Asn Met Asp Met Lys Gln Asp Gln
 65                  70                  75                  80

Arg Leu Thr Val Leu Leu Asn Lys Lys Asp Lys His Leu Ser Leu Arg
                 85                  90                  95

Ile Ala Asp Thr Gln Thr Gly Asp Ser Ala Ile Tyr Phe Cys Ala Glu
            100                 105                 110

Ser Lys Glu Thr Arg Leu Met Phe Gly Asp Gly Thr Gln Leu Val Val
            115                 120                 125

Lys Pro Asn Ile Gln Asn Pro Asp Pro Ala Val Tyr Gln Leu Arg Asp
            130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
            210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 3
<211> LENGTH: 21
<212> TYPE: PRT
<213> ORGANISM: Homo sapiens

<400> SEQUENCE: 3

Met Lys Thr Phe Ala Gly Phe Ser Phe Leu Phe Leu Trp Leu Gln Leu
1               5                   10                  15

Asp Cys Met Ser Arg
            20

<210> SEQ ID NO 4
<211> LENGTH: 113
<212> TYPE: PRT
<213> ORGANISM: Homo sapiens

<400> SEQUENCE: 4

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
            20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
 50                  55                  60
```

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
            85                  90                  95

Ile Ala Asp Thr Gln Thr Gly Asp Ser Ala Ile Tyr Phe Cys Ala Glu
            100                 105                 110

Ser

<210> SEQ ID NO 5
<211> LENGTH: 6
<212> TYPE: PRT
<213> ORGANISM: Homo sapiens

<400> SEQUENCE: 5

Asp Ser Ser Ser Thr Tyr
1               5

<210> SEQ ID NO 6
<211> LENGTH: 3
<212> TYPE: PRT
<213> ORGANISM: Homo sapiens

<400> SEQUENCE: 6

Ile Phe Ser
1

<210> SEQ ID NO 7
<211> LENGTH: 11
<212> TYPE: PRT
<213> ORGANISM: Homo sapiens

<400> SEQUENCE: 7

Cys Ala Glu Ser Lys Glu Thr Arg Leu Met Phe
1               5                   10

<210> SEQ ID NO 8
<211> LENGTH: 14
<212> TYPE: PRT
<213> ORGANISM: Homo sapiens

<400> SEQUENCE: 8

Arg Leu Met Phe Gly Asp Gly Thr Gln Leu Val Val Lys Pro
1               5                   10

<210> SEQ ID NO 9
<211> LENGTH: 141
<212> TYPE: PRT
<213> ORGANISM: Homo sapiens

<400> SEQUENCE: 9

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

```
Ile Ile Pro Glu Asp Thr Phe Phe Pro Ser Pro Glu Ser Ser Cys Asp
            85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Lys Val Ala
            115                 120                 125

Gly Phe Asn Leu Leu Met Thr Leu Arg Leu Trp Ser Ser
    130                 135                 140

<210> SEQ ID NO 10
<211> LENGTH: 318
<212> TYPE: PRT
<213> ORGANISM: Homo sapiens

<400> SEQUENCE: 10

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
            85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg Ala Gly Gly His Glu Gln
            115                 120                 125

Phe Phe Gly Pro Gly Thr Arg Leu Thr Val Leu Glu Asp Leu Lys Asn
    130                 135                 140

Val Phe Pro Pro Glu Val Ala Val Phe Glu Pro Ser Glu Ala Glu Ile
145                 150                 155                 160

Ser His Thr Gln Lys Ala Thr Leu Val Cys Leu Ala Thr Gly Phe Tyr
            165                 170                 175

Pro Asp His Val Glu Leu Ser Trp Trp Val Asn Gly Lys Glu Val His
            180                 185                 190

Ser Gly Val Ser Thr Asp Pro Gln Pro Leu Lys Glu Gln Pro Ala Leu
            195                 200                 205

Asn Asp Ser Arg Tyr Cys Leu Ser Ser Arg Leu Arg Val Ser Ala Thr
    210                 215                 220

Phe Trp Gln Asn Pro Arg Asn His Phe Arg Cys Gln Val Gln Phe Tyr
225                 230                 235                 240

Gly Leu Ser Glu Asn Asp Glu Trp Thr Gln Asp Arg Ala Lys Pro Val
            245                 250                 255

Thr Gln Ile Val Ser Ala Glu Ala Trp Gly Arg Ala Asp Cys Gly Phe
            260                 265                 270

Thr Ser Glu Ser Tyr Gln Gln Gly Val Leu Ser Ala Thr Ile Leu Tyr
            275                 280                 285

Glu Ile Leu Leu Gly Lys Ala Thr Leu Tyr Ala Val Leu Val Ser Ala
            290                 295                 300

Leu Val Leu Met Ala Met Val Lys Arg Lys Asp Ser Arg Gly
305                 310                 315
```

```
<210> SEQ ID NO 11
<211> LENGTH: 25
<212> TYPE: PRT
<213> ORGANISM: Homo sapiens

<400> SEQUENCE: 11

Met Leu Leu Leu Leu Leu Leu Gly Pro Gly Ile Ser Leu Leu Leu
1               5                   10                  15

Pro Gly Ser Leu Ala Gly Ser Gly Leu
            20                  25

<210> SEQ ID NO 12
<211> LENGTH: 122
<212> TYPE: PRT
<213> ORGANISM: Homo sapiens

<400> SEQUENCE: 12

Met Leu Leu Leu Leu Leu Leu Gly Pro Gly Ile Ser Leu Leu Leu
1               5                   10                  15

Pro Gly Ser Leu Ala Gly Ser Gly Leu Gly Ala Val Val Ser Gln His
            20                  25                  30

Pro Ser Trp Val Ile Cys Lys Ser Gly Thr Ser Val Lys Ile Glu Cys
        35                  40                  45

Arg Ser Leu Asp Phe Gln Ala Thr Thr Met Phe Trp Tyr Arg Gln Phe
    50                  55                  60

Pro Lys Gln Ser Leu Met Leu Met Ala Thr Ser Asn Glu Gly Ser Lys
65                  70                  75                  80

Ala Thr Tyr Glu Gln Gly Val Glu Lys Asp Lys Phe Leu Ile Asn His
                85                  90                  95

Ala Ser Leu Thr Leu Ser Thr Leu Thr Val Thr Ser Ala His Pro Glu
            100                 105                 110

Asp Ser Ser Phe Tyr Ile Cys Ser Ala Arg
        115                 120

<210> SEQ ID NO 13
<211> LENGTH: 6
<212> TYPE: PRT
<213> ORGANISM: Homo sapiens

<400> SEQUENCE: 13

Asp Phe Gln Ala Thr Thr
1               5

<210> SEQ ID NO 14
<211> LENGTH: 7
<212> TYPE: PRT
<213> ORGANISM: Homo sapiens

<400> SEQUENCE: 14

Ser Asn Glu Gly Ser Lys Ala
1               5

<210> SEQ ID NO 15
<211> LENGTH: 12
<212> TYPE: PRT
<213> ORGANISM: Homo sapiens

<400> SEQUENCE: 15

Cys Ser Ala Arg Ala Gly Gly His Glu Gln Phe Phe
1               5                   10
```

<210> SEQ ID NO 16
<211> LENGTH: 13
<212> TYPE: PRT
<213> ORGANISM: Homo sapiens

<400> SEQUENCE: 16

Glu Gln Phe Phe Gly Pro Gly Thr Arg Leu Thr Val Leu
1               5                   10

<210> SEQ ID NO 17
<211> LENGTH: 179
<212> TYPE: PRT
<213> ORGANISM: Homo sapiens

<400> SEQUENCE: 17

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 18
<211> LENGTH: 20
<212> TYPE: PRT
<213> ORGANISM: Homo sapiens

<400> SEQUENCE: 18

Val Ile Gly Phe Arg Ile Leu Leu Leu Lys Val Ala Gly Phe Asn Leu
1               5                   10                  15

Leu Met Thr Leu
            20

<210> SEQ ID NO 19
<211> LENGTH: 23
<212> TYPE: PRT
<213> ORGANISM: Homo sapiens

<400> SEQUENCE: 19

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 20
<211> LENGTH: 274
<212> TYPE: PRT
<213> ORGANISM: Homo sapiens

<400> SEQUENCE: 20

Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190

Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
    210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
            260                 265                 270

Ser Ser

<210> SEQ ID NO 21
<211> LENGTH: 311
<212> TYPE: PRT
<213> ORGANISM: Homo sapiens

<400> SEQUENCE: 21

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

```
Lys Thr Gly Gln Ser Met Thr Leu Gln Cys Ala Gln Asp Met Asn His
             35                  40                  45
Glu Tyr Met Ser Trp Tyr Arg Gln Asp Pro Gly Met Gly Leu Arg Leu
 50                  55                  60
Ile His Tyr Ser Val Gly Ala Gly Ile Thr Asp Gln Gly Glu Val Pro
 65                  70                  75                  80
Asn Gly Tyr Asn Val Ser Arg Ser Thr Thr Glu Asp Phe Pro Leu Arg
                 85                  90                  95
Leu Leu Ser Ala Ala Pro Ser Gln Thr Ser Val Tyr Phe Cys Ala Ser
                100                 105                 110
Ser Tyr Val Gly Asn Thr Gly Glu Leu Phe Phe Gly Glu Gly Ser Arg
            115                 120                 125
Leu Thr Val Leu Glu Asp Leu Lys Asn Val Phe Pro Pro Glu Val Ala
        130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
                165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
        195                 200                 205
Ser Ser Arg Leu Arg Val Ser Ala Thr Phe Trp Gln Asn Pro Arg Asn
210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
                245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
        275                 280                 285
Thr Leu Tyr Ala Val Leu Val Ser Ala Leu Val Leu Met Ala Met Val
290                 295                 300
Lys Arg Lys Asp Ser Arg Gly
305                 310

<210> SEQ ID NO 22
<211> LENGTH: 36
<212> TYPE: DNA
<213> ORGANISM: Homo sapiens

<400> SEQUENCE: 22
ggaattccat atgagtcaac aaggagaaga agatcc                              36

<210> SEQ ID NO 23
<211> LENGTH: 36
<212> TYPE: DNA
<213> ORGANISM: Homo sapiens

<400> SEQUENCE: 23
ttgtcagtcg acttagagtc tctcagctgg tacacg                              36

<210> SEQ ID NO 24
<211> LENGTH: 36
<212> TYPE: DNA
<213> ORGANISM: Homo sapiens
```

<400> SEQUENCE: 24
tctctcatat ggatggtgga attactcaat ccccaa                36

<210> SEQ ID NO 25
<211> LENGTH: 32
<212> TYPE: DNA
<213> ORGANISM: Homo sapiens

<400> SEQUENCE: 25
tagaaaccgg tggccaggca caccagtgtg gc                    32

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

-continued

<210> SEQ ID NO 35

<400> SEQUENCE: 35

000

<210> SEQ ID NO 36

<400> SEQUENCE: 36

000

<210> SEQ ID NO 37
<211> LENGTH: 9
<212> TYPE: PRT
<213> ORGANISM: Homo sapiens

<400> SEQUENCE: 37

Ala Ile Gln Glu Ile Leu Thr Gln Val
1               5

<210> SEQ ID NO 38
<211> LENGTH: 9
<212> TYPE: PRT
<213> ORGANISM: Homo sapiens

<400> SEQUENCE: 38

Lys Ala Gln Glu Ile Leu Thr Gln Val
1               5

<210> SEQ ID NO 39
<211> LENGTH: 9
<212> TYPE: PRT
<213> ORGANISM: Homo sapiens

<400> SEQUENCE: 39

Lys Ile Ala Glu Ile Leu Thr Gln Val
1               5

<210> SEQ ID NO 40
<211> LENGTH: 9
<212> TYPE: PRT
<213> ORGANISM: Homo sapiens

<400> SEQUENCE: 40

Lys Ile Gln Ala Ile Leu Thr Gln Val
1               5

<210> SEQ ID NO 41
<211> LENGTH: 9
<212> TYPE: PRT
<213> ORGANISM: Homo sapiens

<400> SEQUENCE: 41

Lys Ile Gln Glu Ala Leu Thr Gln Val
1               5

<210> SEQ ID NO 42
<211> LENGTH: 9
<212> TYPE: PRT
<213> ORGANISM: Homo sapiens

<400> SEQUENCE: 42

Lys Ile Gln Glu Ile Ala Thr Gln Val
1               5

```
<210> SEQ ID NO 43
<211> LENGTH: 9
<212> TYPE: PRT
<213> ORGANISM: Homo sapiens

<400> SEQUENCE: 43

Lys Ile Gln Glu Ile Leu Ala Gln Val
1               5

<210> SEQ ID NO 44
<211> LENGTH: 9
<212> TYPE: PRT
<213> ORGANISM: Homo sapiens

<400> SEQUENCE: 44

Lys Ile Gln Glu Ile Leu Thr Ala Val
1               5

<210> SEQ ID NO 45
<211> LENGTH: 9
<212> TYPE: PRT
<213> ORGANISM: Homo sapiens

<400> SEQUENCE: 45

Lys Ile Gln Glu Ile Leu Thr Gln Ala
1               5
```